US012793213B2

(12) United States Patent
Iizuka et al.

(10) Patent No.: US 12,793,213 B2
(45) Date of Patent: Nov. 10, 2026

(54) IMAGE PROCESSING APPARATUS TO DETERMINE REGIONS OF MEDICAL SIGNIFICANCE IN A MEDICAL IMAGE

(71) Applicant: CANON KABUSHIKI KAISHA, Tokyo (JP)

(72) Inventors: Yoshio Iizuka, Yokohama (JP); Yuki Nagato, Utsunomiya (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 409 days.

(21) Appl. No.: 18/446,601

(22) Filed: Aug. 9, 2023

(65) Prior Publication Data

US 2024/0054643 A1 Feb. 15, 2024

(30) Foreign Application Priority Data

Aug. 9, 2022 (JP) ................................ 2022-127470

(51) Int. Cl.
*G06T 7/00* (2017.01)
*G06T 7/62* (2017.01)
(Continued)

(52) U.S. Cl.
CPC .............. *G06T 7/0012* (2013.01); *G06T 7/62* (2017.01); *G06V 10/25* (2022.01); *G06V 10/28* (2022.01); *G06V 10/758* (2022.01); *G16H 30/40* (2018.01)

(58) Field of Classification Search
CPC ........... G06T 7/0012; G06T 7/62; G06T 7/00; G06T 7/11; G06T 7/12; G06T 2207/10081; G06T 2207/10088; G06T 2207/10104; G06T 2207/10108; G06V 10/25; G06V 10/28; G06V 10/758; G06V 10/26; G06V 10/82; G06V 2201/031; G16H 30/40; G16H 40/67; G16H 50/20; G16H 50/70
See application file for complete search history.

(56) References Cited

U.S. PATENT DOCUMENTS

| | | | | |
|---|---|---|---|---|
| 2019/0046127 A1* | 2/2019 | Furukawa | .............. | A61B 6/032 |
| 2019/0258892 A1 | 8/2019 | Chen | | |

(Continued)

FOREIGN PATENT DOCUMENTS

| | | |
|---|---|---|
| JP | 2001-218051 A | 8/2001 |
| JP | 2009-273771 A | 11/2009 |

(Continued)

*Primary Examiner* — Siamak Harandi
(74) *Attorney, Agent, or Firm* — Oblon, McClelland, Maier & Neustadt, L.L.P.

(57) ABSTRACT

An image processing apparatus according to embodiments extracts a region of interest including a specified point on medical image data. The image processing apparatus includes processing circuitry. The processing circuitry extracts a first extraction region estimated as the region of interest from first partial image data included in a first processing range that includes the specified point of the medical image data. The processing circuitry extracts a second extraction region estimated as the region of interest from second partial image data included in a second processing range that is in contact with an edge portion of the first processing range or that includes at least a part of the edge portion, from the medical image data when the first extraction region is determined as a part of the region of interest.

24 Claims, 15 Drawing Sheets

(51) Int. Cl.

| | |
|---|---|
| ***G06V 10/25*** | (2022.01) |
| ***G06V 10/26*** | (2022.01) |
| ***G06V 10/28*** | (2022.01) |
| ***G06V 10/75*** | (2022.01) |
| ***G16H 30/40*** | (2018.01) |

(56) References Cited

U.S. PATENT DOCUMENTS

| | | | | |
|---|---|---|---|---|
| 2019/0392578 | A1 | 12/2019 | Chukka et al. | |
| 2020/0074634 | A1 | 3/2020 | Kecskemethy et al. | |
| 2020/0111214 | A1 * | 4/2020 | Chen | G06T 7/143 |
| 2020/0364852 | A1 | 11/2020 | Park | |
| 2021/0201485 | A1 | 7/2021 | Chukka et al. | |
| 2021/0407655 | A1 | 12/2021 | Ohyu | |

FOREIGN PATENT DOCUMENTS

| | | | |
|---|---|---|---|
| JP | 2016-193295 | A | 11/2016 |
| JP | 2017-224061 | A | 12/2017 |
| JP | 2018-77667 | A | 5/2018 |
| JP | 2020-502534 | A | 1/2020 |
| JP | 2020-516427 | A | 6/2020 |
| JP | 2020-149684 | A | 9/2020 |
| JP | 2020-185374 | A | 11/2020 |
| JP | 6948959 | B2 | 10/2021 |

* cited by examiner

IMAGE PROCESSING APPARATUS TO DETERMINE REGIONS OF MEDICAL SIGNIFICANCE IN A MEDICAL IMAGE

CROSS-REFERENCE TO RELATED APPLICATIONS

This application is based upon and claims the benefit of priority from Japanese Patent Application No. 2022-127470, filed on Aug. 9, 2022; the entire contents of which are incorporated herein by reference.

FIELD

Embodiments disclosed in the present specification and drawings relate to an image processing apparatus, an image processing method, and a recording medium.

BACKGROUND

There has been a technique of extracting a region of interest of various sizes captured in medical image data. For example, a region of interest is a lesion area, such as tumor. The volume of a tumor can be equal to or smaller than 0.01 $cm^3$, or can be equal to or larger than 100 $cm^3$, and the size of tumor can vary across orders of magnitude to be in a various sizes. For example, region extraction using deep neural networks (DNN) is generally highly accurate, but only images in a fixed size can be input thereto. If the fixed size is too large with respect to the region of interest, the accuracy of extracting a region of interest, the size of which is too small with respect to the fixed size decreases. On the other hand, if the fixed size is too small with respect to a region of interest, a region of interest, the size of which is too large with respect to the fixed size can be extracted only partially.

Furthermore, there has been a technique of extracting a region of interest by dividing entire image data into plural partial regions in a fixed size, and by processing all of the partial regions. Because the number of subregions to be processed is significantly large in this technique, the computational time becomes significantly long.

DETAILED DESCRIPTION

One of challenges to be achieved by embodiments disclosed in the present specification and drawings is to extract (segment) a region of interest captured in medical image data highly accurately and at high speed. However, challenges to be solved by the embodiment disclosed in the present specification and drawings are not limited to the above challenge. Challenges corresponding to respective effects produced by respective configurations described in embodiments described later can be regarded as other challenges.

An image processing apparatus according to an embodiment extracts a region of interest including a specified point on medical image data. The image processing apparatus includes processing circuitry. The processing circuitry extracts a first extraction region that is estimated as the region of interest from first partial image data included in a first processing range including the specified point of the medical image data. The processing circuitry extracts a second extraction region that is estimated as the region of interest from second partial image data included in a second processing range that is in contact with an edge portion of the first processing range or that includes at least a part of the edge portion, from the medical image data when the first extraction region is a part of the region of interest.

Hereinafter, respective embodiments and respective modifications of an image processing apparatus, an image processing method, and a program will be explained in detail with reference to the drawings. The embodiments can be combined with a conventional technique, another embodiment or modification, within a range not causing contradiction in contents. Similarly, the modification can be combined with a conventional technique, an embodiment, or another modification within a range not causing contradiction in contents. Moreover, in the following explanation, common symbols are assigned to like components, and duplicated explanation may be omitted.

First Embodiment

Figure 1:
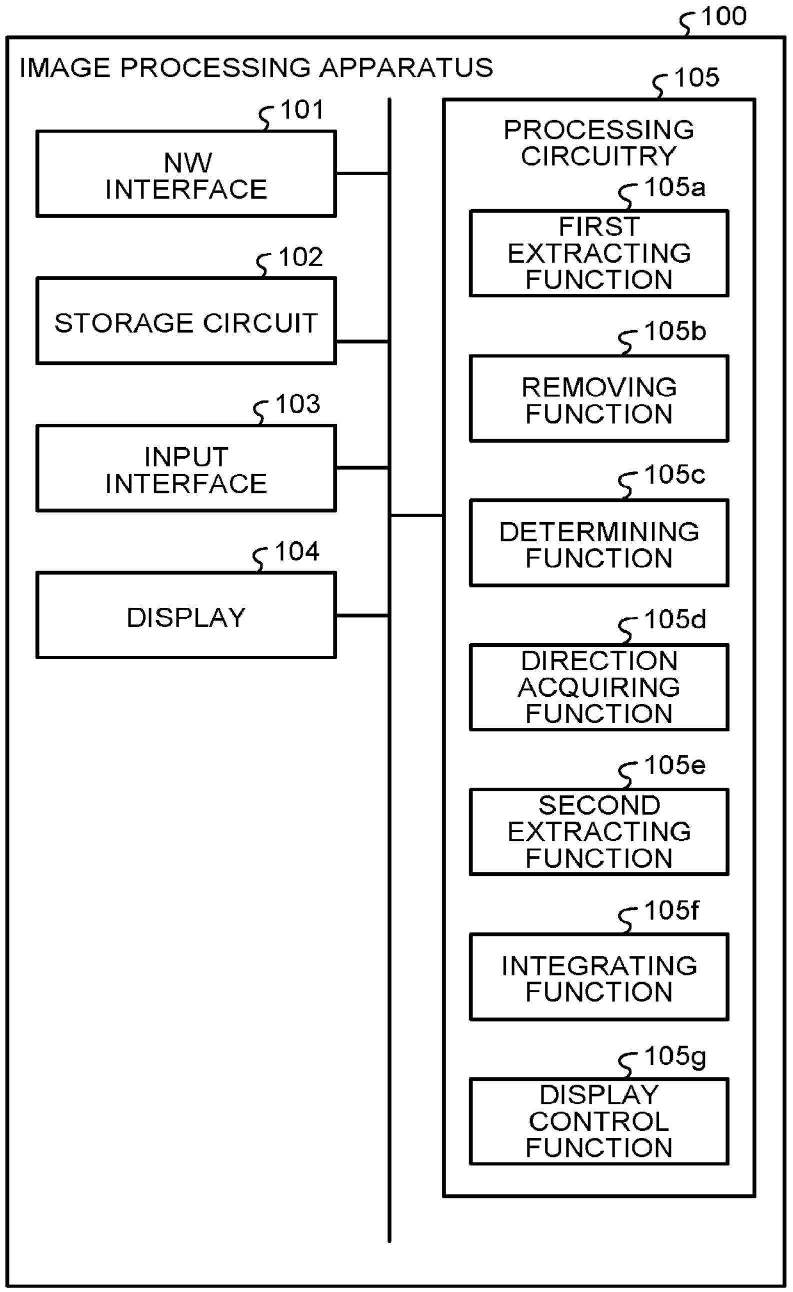
FIG. 1 is a diagram illustrating an example of a configuration of an image processing apparatus according to a first embodiment.

FIG. 1 is a diagram illustrating an example of a configuration of an image processing apparatus 100 according to a first embodiment. For example, the image processing apparatus 100 is installed in medical facilities, such as hospitals and clinics. The image processing apparatus 100 is connected to a modality through a network in a communication-enabled manner.

The modality is, for example, a medical-image generating apparatus that generates medical image data, such as X-ray computed tomography (CT) apparatus, ultrasound diagnostic apparatus, magnetic resonance imaging (MRI) apparatus, positron emission tomography (PET) apparatus, or single photon emission computed tomography (SPECT) apparatus. For example, the modality generates medical image data in which a region of interest of a subject (patient) is captured (medical image data showing a region of interest). The region of interest is, for example, a region of a lesion, such as tumor. The medical image data is three-dimensional medical image data or two-dimensional medical image data. The medical image data is, for example, CT image data, ultrasound image data, MR image data, PET image data, SPECT image data, and the like. The modality transmits generated medical image data to the image processing apparatus 100 through a network.

The image processing apparatus 100 acquires medical image data from the modality connected through a network, performs image processing with respect to the medical image data, and displays a result of the image processing. The image processing apparatus 100 may analyze the result of image processing (for example, measure the volume of a region of interest). Furthermore, the image processing apparatus 100 may store the result of image processing in association with medical image data, or may output the result of image processing to an external server. For example, the image processing apparatus 100 extracts a region of interest captured in medical image data, and displays an extraction result. The image processing apparatus 100 is implemented by, for example, a computer device, such as a server and a work station.

As illustrated in FIG. 1, the image processing apparatus 100 includes a network (NW) interface 101, a storage circuit 102, an input interface 103, a display 104, and processing circuitry 105.

The NW interface 101 controls transmission and communication of various kinds of data communicated between the image processing apparatus 100 and other devices (modality and the like) connected to the image processing apparatus 100 through a network. For example, the NW interface 101 is connected to the processing circuitry 105, and receives data transmitted by another device and the like, and transmits the received data and the like to the processing circuitry 105. Specifically, it receives medical image data transmitted by the modality, and transmits the received medical image data to the processing circuitry 105. Moreover, the NW interface 101 receives data transmitted by the processing circuitry 105 and the like, and transmits the received data and the like to another device. For example, the NW interface 101 is implemented by a network card, a network adaptor, a network interface controller (NIC), or the like.

The storage circuit 102 stores various kinds of data and various kinds of programs. Specifically, the storage circuit 102 is connected to the processing circuitry 105, and stores various kinds of data under the control of the processing circuitry 105. For example, the storage circuit 102 stores medical image data under the control of the processing circuitry 105. Furthermore, the storage circuit 102 also has a function as a work memory to temporarily store various kinds of data used for processing performed by the processing circuitry 105. For example, the storage circuit 102 is implemented by a semiconductor memory device, such as a random access memory (RAM) and a flash memory, a hard disk, an optical disk, and the like.

The input interface 103 accepts input operations of various kinds of instructions and various kinds of information from a user of the image processing apparatus 100. Specifically, the input interface 103 is connected to the processing circuitry 105, and converts an input operation received from a user into an electrical signal, to transmit to the processing circuitry 105. For example, the input interface 103 is implemented by a trackball, a switch button, a mouse, a keyboard, a touch pad with which an input operation is performed by touching an operating surface, a touch screen in which a display screen and a touch pad are integrated, a non-contact input interface using an optical sensor, a sound input interface, and the like. In the present specification, the input interface 103 is not limited to one that has physical operating parts, such as a mouse and a keyboard. For example, processing circuitry of an electrical signal that is provided separately from the image processing apparatus 100, and that receives an electrical signal corresponding to an input operation from an external input device and transmits this electrical signal to the processing circuitry 105 is also included in examples of the input interface 103. The processing circuitry is implemented by, for example, a processor. The input interface 103 is an example of an accepting unit.

The display 104 displays various kinds of images, various kinds of information, and various kinds of data. Specifically, the display 104 is connected to the processing circuitry 105, and displays images based on various kinds of image data, various kinds of information, and various kinds of data that are received from the processing circuitry 105. For example, the display 104 displays a medical image based on medical image data. For example, the display 104 is implemented by a liquid crystal monitor, a cathode ray tube monitor, a touch panel, or the like. The display 104 is an example of a display unit.

The processing circuitry 105 controls the entire image processing apparatus 100. For example, the processing circuitry 105 performs various kinds of processing according to an input operation accepted from a user through the input interface 103. The processing circuitry 105 is implemented by, for example, a processor.

Furthermore, upon reception of medical image data transmitted by the NW interface 101, the processing circuitry 105 stores the received medical image data in the storage circuit 102.

For example, as illustrated in FIG. 1, the processing circuitry 105 includes a first extracting function 105*a*, a removing function 105*b*, a determining function 105*c*, a direction acquiring function 105*d*, a second extracting function 105*e*, an integrating function 105*f*, and a display control function 105*g*. The first extracting function 105*a* is an example of a first extracting unit. The removing function 105*b* is an example of a removing unit. The determining function 105*c* is an example of a determining unit. The direction acquiring function 105*d* is an example of a direction acquiring unit. The second extracting function 105*e* is an example of a second extracting unit. The integrating function 105*f* is an example of an integrating unit and an example of a second extracting unit. The display control function 105*g* is an example of a display control unit.

For example, the respective processing functions of the first extracting function 105*a*, the removing function 105*b*, the determining function 105*c*, the direction acquiring function 105*d*, the second extracting function 105*e*, the integrating function 105*f*, and the display control function 105*g*, which are components of the processing circuitry 105 illustrated in FIG. 1, are stored in the storage circuit 102 in a form of computer-executable program. The processing circuitry 105 reads respective programs from the storage circuit 102, and executes the read programs, and thereby implements the functions corresponding to the respective programs. In other words, the processing circuitry 105 that has read the respective programs are to have the respective functions indicated in the processing circuitry 105 in FIG. 1.

As above, a configuration example of the image processing apparatus 100 according to the present embodiment has been explained. According to the present embodiment, the image processing apparatus 100 performs various kinds of processing explained below to be able to extract (segment) a region of interest captured in medical image data highly accurately and at high speed. Hereinafter, a case in which the image processing apparatus 100 performs various kinds of processing with respect to three-dimensional medical image data will be explained. However, the image processing apparatus 100 may perform processing similar to various kinds of processing performed with respect to three-dimensional medical image data, with respect to two-dimensional medical image data. Moreover, drawings referred to in the explanation below can appear to correspond to not three-dimensional but two-dimensional medical image data. However, the respective drawings actually correspond to three-dimensional medical image data.

Figure 2A:
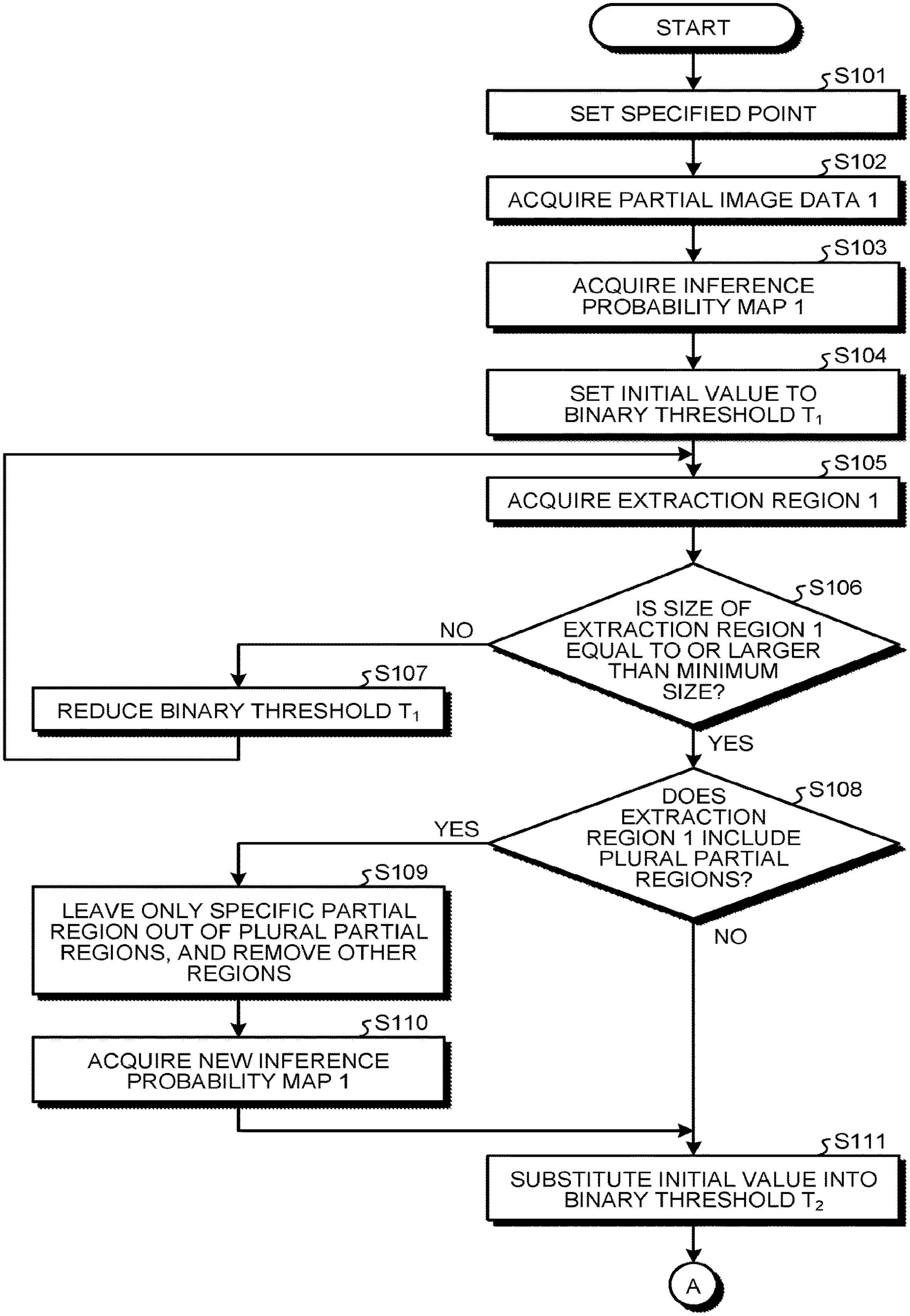
FIG. 2A is a flowchart illustrating a flow of an example of region extraction processing performed by the image processing apparatus according to the first embodiment.
Figure 2B:
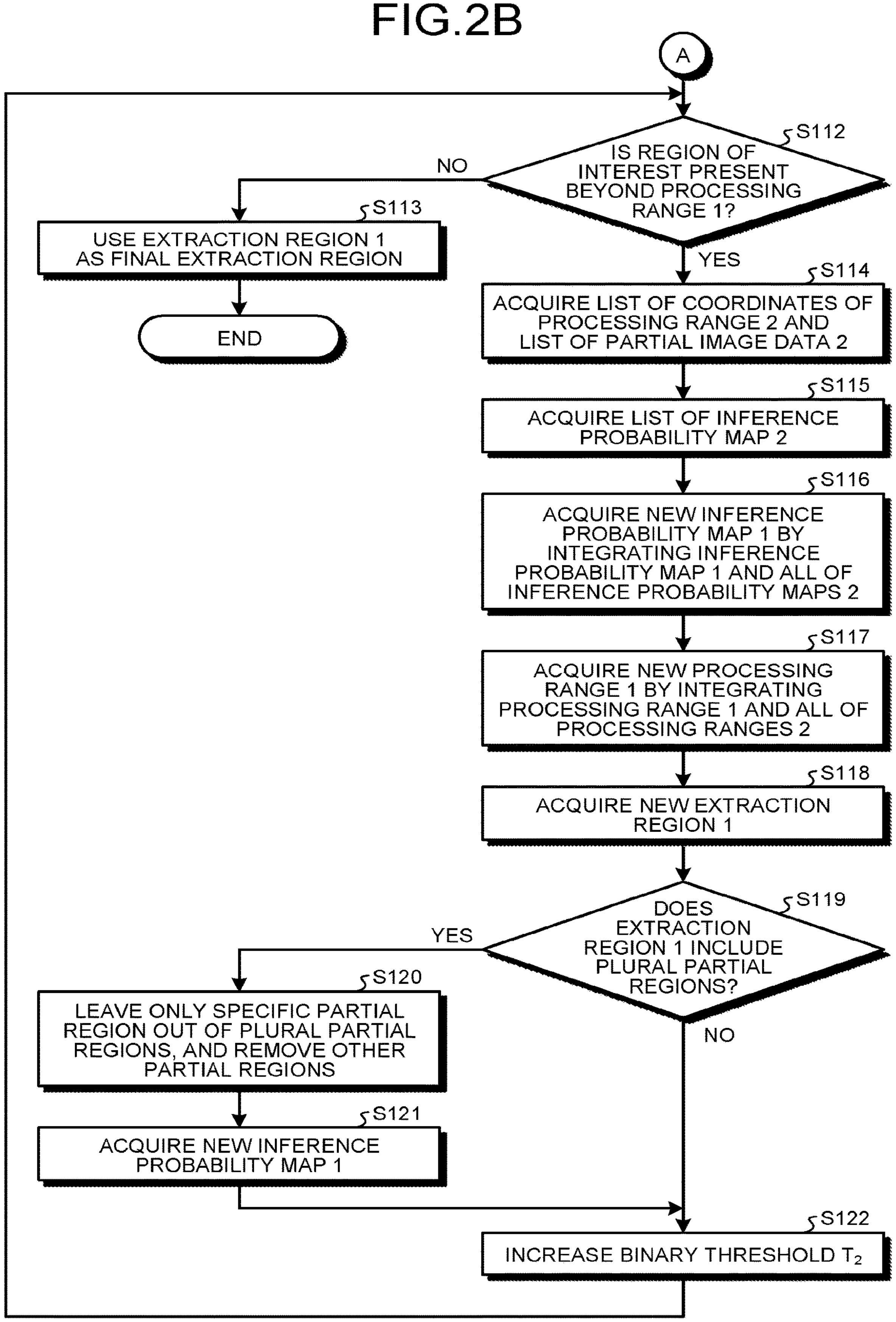
FIG. 2B is a flowchart illustrating a flow of an example of the region extraction processing performed by the image processing apparatus according to the first embodiment.

An example of region extraction processing performed by the image processing apparatus 100 will be explained. The region extraction processing is processing of extracting a region of interest shown in medical image data. The region of interest is a region subject to extraction (extraction subject region). FIG. 2A and FIG. 2B are flowcharts illustrating a flow of the region extraction processing performed by the image processing apparatus 100 according to the first embodiment. The region extraction processing illustrated in FIG. 2A and FIG. 2B is performed when a user inputs an instruction to perform the region extraction processing with respect to medical image data to be processed into the processing circuitry 105 through the input interface 103 in a state in which the medical image data to be processed is stored in the storage circuit 102.

As illustrated in FIG. 2A, the first extracting function 105*a* sets a point in a region of interest shown in three-dimensional medical image data to be processed (region of interest rendered in three-dimensional medical image) as a specified point (step S101).

Figure 3:
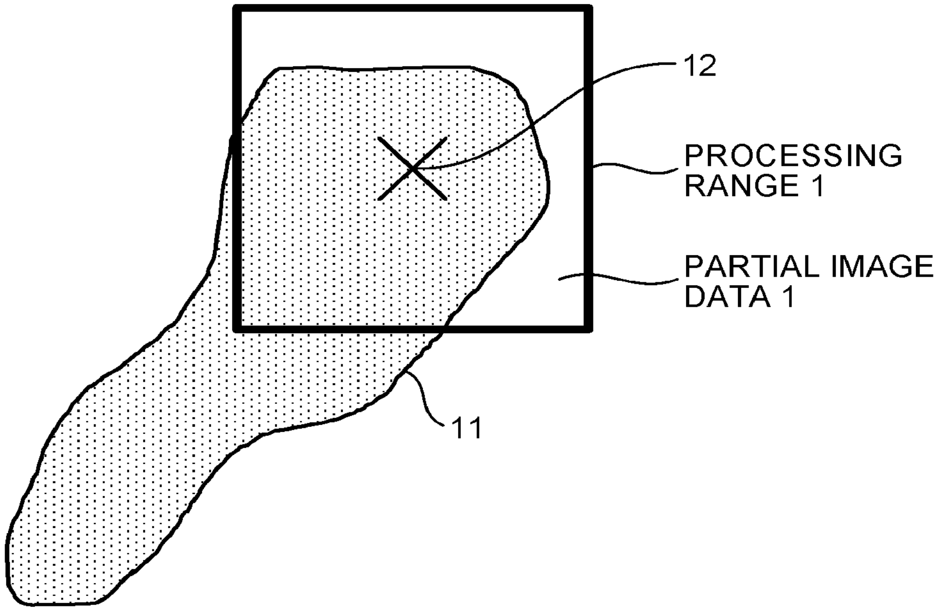
FIG. 3 is a diagram for explaining an example of processing performed by the image processing apparatus according to the first embodiment.

An example of processing at step S101 will be explained. FIGS. 3 to 13 are diagrams for explaining an example of processing performed by the image processing apparatus 100 according to the first embodiment. At step S101, first, the first extracting function 105*a* acquires medical image data to be a subject to be processed stored in the storage circuit 102. As illustrated in FIG. 3, the first extracting function 105*a* sets a point in a region of interest 11 captured in medical image data as a specified point 12. As a method of setting the specified point 12, various methods are considered. For example, the first extracting function 105*a* displays a medical image based on the medical image data on the display 104. Thus, the region of interest 11 captured in the medical image data (medical image) is displayed on the display 104. A user, such as doctor, specifies a position of the specified point 12 on the region of interest 11 by operating the input interface 103 while observing the region of interest 11. The first extracting function 105*a* accepts the position specified by the user as a position of the specified point 12. The first extracting function 105*a* sets the accepted position of the specified point 12. Thus, the specified point 12 is set. In the present embodiment, the image processing apparatus 100 extracts the region of interest 11 including the specified point 12 on the medical image data.

The first extracting function 105*a* may automatically detects a lesion candidate point from the medical image data by using a conventional technique, and may set the lesion candidate point automatically detected as the specified point 12. The lesion candidate point herein is a point to be a candidate in a lesion area.

Next, the first extracting function 105*a* sets, as illustrated in FIG. 3, a three-dimensional image range of a predetermined fixed size (fixed size 1) that includes the specified point 12 on the medical image data as a processing range 1, acquires coordinates of the processing range 1, and acquires three-dimensional partial image data 1 in the processing range 1 (step S102). The processing range 1 is, for example, a range indicated by a cube in a predetermined size in which the specified point 12 is set at a center position. That is, the processing range 1 is a range defined by six planes of a cube in a predetermined size. At step S102, because the length of one side of the processing range 1 is determined in advance and because the respective directions of 12 sides of the processing range 1 in an image coordinate system that is a three-dimensional orthogonal (X, Y, Z) coordinate system, the first extracting function 105*a* may acquire coordinates of one vertex of the processing range 1 as coordinates that can define the processing range 1. The shape of the processing range 1 may be a shape other than cube. For example, the processing range 1 may be a range indicated by a cuboid.

Figure 4:
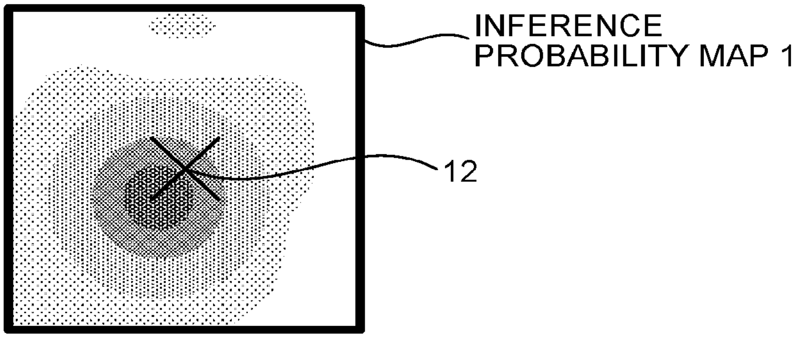
FIG. 4 is a diagram for explaining an example of processing performed by the image processing apparatus according to the first embodiment.

Next, the first extracting function 105*a* acquires an inference probability map 1 that corresponds to the partial image data 1 by using a pre-trained inference model for segmentation as a region extraction means to extract a region of interest from the medical image data (step S103). An example of processing at step S103 will be explained. For example, as the inference model as described above, "3D U-Net" is used. "U-Net" is a publicly known inference model (constituted of an encoder and a decoder) for segmentation that uses a deep neural network technique. In the present embodiment, "U-Net" that is generated to receive a three-dimensional image as input data and outputs a three-dimensional probability map corresponding to the input data is called "3D U-Net". The inference model is stored in the storage circuit 102 in advance. The inference model is a neural network that outputs the inference probability map 1, which is a map indicating a probability (inference probability) that respective pixels of the partial image data 1 are pixels included in the region of interest 11 as illustrated in FIG. 4, upon reception of the partial image data 1 of a predetermined fixed size as an input. The probability is a value from 0.0 to 1.0.

At step S103, the first extracting function 105*a* acquires an inference model stored in the storage circuit 102. The first extracting function 105*a* inputs the partial image data to the acquired inference model, and acquires the inference probability map 1 output from the inference model.

At step S103, the first extracting function 105*a* may resize (isotropically rescale) the partial image data to make pixel spacing of the partial image data 1 be 1×1×1 [mm], and may input the isotropically rescaled image data obtained as a result of resizing to the inference model. In this case, coordinates of the specified point 12 are converted into coordinates corresponding to the isotropically rescaled image data. Moreover, in this case, the size of the partial image data 1 is to be a size determined in advance in the isotropically rescaled image data. For example, when pixel spacing of an original image is 0.5×0.5×2.0 [mm] where the size of the partial image data 1 in the isotropically rescaled image data is m×m×m [pixels], the partial image data 1 of 2m×2m×(m/2) [pixels] is acquired.

Next, the first extracting function 105*a* sets an initial value "0.5" to a threshold (binary threshold) $T_1$ that is used at step S105 described later (step S104). The initial value is not limited to "0.5". As long as it is larger than 0.0 and smaller than 1.0, any value may be used as the initial value.

Next, the first extracting function 105*a* performs binary processing with respect to the inference probability map 1 acquired at step S103 using the binary threshold $T_1$, to acquire the extraction region 1 (step S105).

Figure 5:
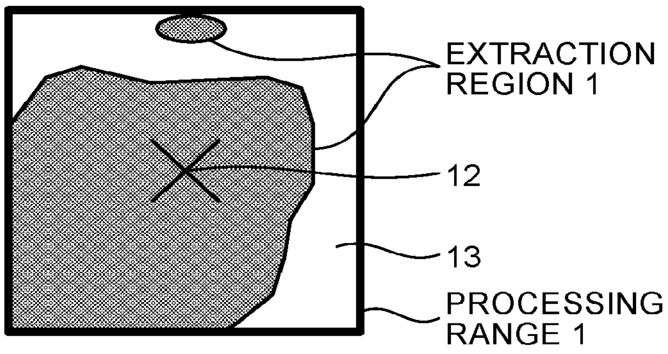
FIG. 5 is a diagram for explaining an example of processing performed by the image processing apparatus according to the first embodiment.

An example of processing at step S105 will be explained. At step S105, the first extracting function 105*a* acquires three-dimensional binary image data 13 illustrated in FIG. 5 by performing binary processing with respect to the inference probability map 1 using the binary threshold $T_1$. That is, to a pixel of the binary image data 13 corresponding to a pixel to which a value equal to or larger than the binary threshold $T_1$ is set in the inference probability map 1, a value indicating the inside the extraction region 1 (value corresponding to black in the example in FIG. 5) is set. Moreover, to a pixel of the binary image data 13 corresponding to a pixel to which a value smaller than the binary threshold $T_1$ is set in the inference probability map 1, a value indicating the outside the extraction region 1 (value corresponding to white in the example in FIG. 5) is set. The first extracting function 105*a* then extracts a region constituted of pixels to which the value indicating the inside of the extraction region 1 is set out of the entire pixels of the binary image data 13 as the extraction region 1 as illustrated in FIG. 5. In the example in FIG. 5, a case in which the first extracting function 105*a* has extracted the extraction region 1 including two partial regions from the binary image data 13 is illustrated. Moreover, a method of acquiring the extraction region 1 from the inference probability map 1 is not limited to the method described above. The first extracting function 105*a* may acquire the extraction region 1 by using an arbitrary method.

Next, the first extracting function 105*a* calculates the size of the extraction region 1 extracted at step S105, and determines whether the calculated size is equal to or larger than a predetermined size (minimum size) (step S106). For example, as the size of the extraction region 1, the number of pixels or the volume of the extraction region 1 can be considered. Furthermore, the minimum size may be set by a user. When the volume is used as the size of the extraction region 1, the minimum size is 10 $mm^3$ as one example.

When the size of the extraction region 1 is equal to or larger than the minimum size (step S106: YES), the first extracting function 105*a* proceeds to step S108. On the other hand, when the size of the extraction region 1 is smaller than the minimum size (step S106: NO), the first extracting function 105*a* reduces the binary threshold $T_1$ in accordance with a predetermined rule (step S107). The predetermined rule is, for example, a rule of multiplying the binary threshold $T_1$ by "0.2". Furthermore, the first extracting function 105*a* may perform readjustment of the binary threshold $T_1$ based on other methods. For example, when the specified point 12 is not included in the extraction region 1, similar processing may be performed. This enables the specified point 12 to be included in the region of interest. Moreover, the first extracting function 105*a* may determine the binary threshold $T_1$ based on the specified point 12 such that the specified point 12 is included in the region of interest. For example, the first extracting function 105*a* may determine the binary threshold $T_1$ based on a value of the inference probability map 1 at the specified point 12 and its adjacent positions. As one example, the first extracting function 105*a* may determine a value smaller than a value of the inference probability map 1 at the specified point 12 or its adjacent position as the binary threshold $T_1$.

The first extracting function 105*a* then returns to step S105. In this case, at step S105, the first extracting function 105*a* performs binary processing with respect to the inference probability map 1 acquired at step S103 using the binary threshold $T_1$ reduced at step S107, to acquire the extraction region 1. The first extracting function 105*a* then performs the processing at step S106 and later again. When the binary threshold $T_1$ becomes smaller than a predetermined minimum threshold (for example, 0.02), the first extracting function 105*a* sets the minimum threshold to the binary threshold $T_1$, and proceeds to step S108 from step S107, without returning to step S105 from step S107.

By the processing at step S106 and S107, it is possible to increase a probability that the extraction region 1 equal to or larger than the minimum size is extracted. The processing at step S106 and S107 can be omitted. That is, the first extracting function 105*a* may perform processing at step S108 and later described later after performing the processing at step S105, without performing the processing at step S106 and S107.

As described above, the first extracting function 105*a* extracts the extraction region 1 estimated as the region of interest 11 from the partial image data 1 included in the processing range 1 that includes the specified point 12 of the medical image data. The processing range 1 is one example of a first processing range. The partial image data 1 is one example of first partial image data. The extraction region 1 is one example of a first extraction region. Furthermore, the first extracting function 105*a* acquires the inference probability map 1 that is acquired by calculating a probability that respective pixels of the partial image data 1 are a pixel included in the region of interest 11, and extracts the extraction region 1 by binarizing the inference probability map 1. The inference probability map 1 is one example of a first inference probability map.

Moreover, as described above, when the size of the extraction region 1 is smaller than a predetermined size (minimum size), the first extracting function 105*a* reduces the binary threshold $T_1$ used for binarization of the inference probability map 1 in accordance with a predetermined rule, and binarizes the inference probability map 1 again with the reduced binary threshold $T_1$, to thereby extract the extraction region 1.

Next, the removing function 105*b* determines whether the extraction region 1 includes plural partial regions that are not connected to one another step S108). Fore example, in the case illustrated in FIG. 5, the removing function 105*b* determines that the extraction region 1 includes two partial regions that are not connected to each other (step S108: YES).

when the extraction region 1 does not include plural partial regions that are not connected to each other (step S108: NO), that is, when the extraction region 1 is a single region, the removing function 105*b* proceeds to step S111.

On the other hand, when the extraction region 1 includes plural partial regions that are not connected to each other (step S108: YES), the removing function 105*b* leaves only a specific partial region out of the plural partial regions, and removes the other partial regions (step S109).

Figure 6:
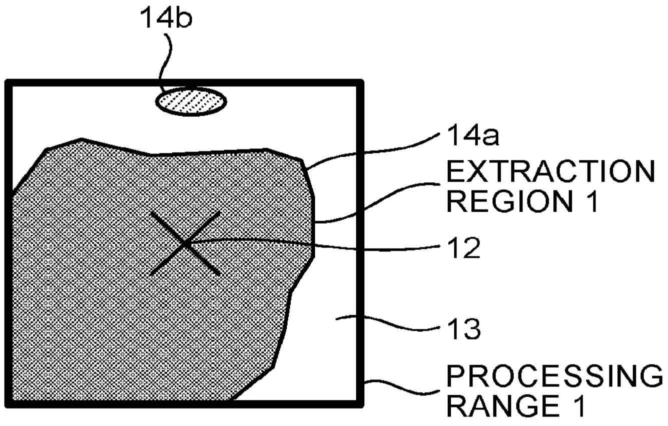
FIG. 6 is a diagram for explaining an example of processing performed by the image processing apparatus according to the first embodiment.

An example of processing at step S109 will be explained. For example, at step S109, the removing function 105*b* leaves only a partial region including the specified point 12 out of the plural partial regions, and removes the other partial regions. Thus, the removing function 105*b* acquires the partial region including the specified point 12 as the new extraction region 1. For example, as illustrated in FIG. 6, at step S109, the removing function 105*b* leaves only a partial region 14*a* that includes the specified point 12 therein out of plural partial regions 14*a* and 14*b*, and removes the other partial region 14*b*. That is, when the extraction region 1 includes the plural partial regions 14*a* and 14*b* that are not connected to each other, the removing function 105*b* removes the partial region 14*b* that does not include the specified point 12 out of the plural partial regions 14*a* and 14*b*. Thus, the removing function 105*b* acquires the partial region 14*a* as the new extraction region 1.

At step S109, the removing function 105*b* may leave a partial region, the center of gravity of which is the closest to the specified point 12 out of plural partial regions, and may remove other partial regions. That is, when the extraction region 1 includes plural partial regions that are not connected to each other, the removing function 105*b* calculates the center of gravity of each of the plural partial regions, and removes the partial regions other than the partial region, the center of gravity of which is the closest to the specified point 12. Thus, the removing function 105*b* acquires the partial region, the center of gravity of which is the closest to the specified point 12 as the new extraction region 1. Moreover, when the extraction region 1 includes plural partial regions that are not connected to each other, the removing function 105*b* may remove partial regions other than a partial region, the center of bounding rectangle of which is the closest to the specified point 12 out of the plural partial regions. Thus, the removing function 105*b* acquires a partial region, the center of bounding rectangle of which is the closest to the center of bounding rectangles of plural partial regions, or a partial region including the center of the bounding rectangle as the new extraction region 1.

Furthermore, at step S109, the removing function 105*b* may remove partial regions other than a partial region largest in size, out of the plural partial regions. Thus, the removing function 105*b* acquires the partial region that is largest in size as the new extraction region 1.

By the processing at step S109, it is possible to remove an unnecessary partial region that has a high possibility of erroneous extraction of extracting a region that is not the region of interest 11 by mistake. Moreover, as a result of removing the unnecessary partial region having a high possibility of erroneous extraction, it is possible to suppress increase of computational time because of an increased processing range based on the region erroneously extracted.

Figure 7:
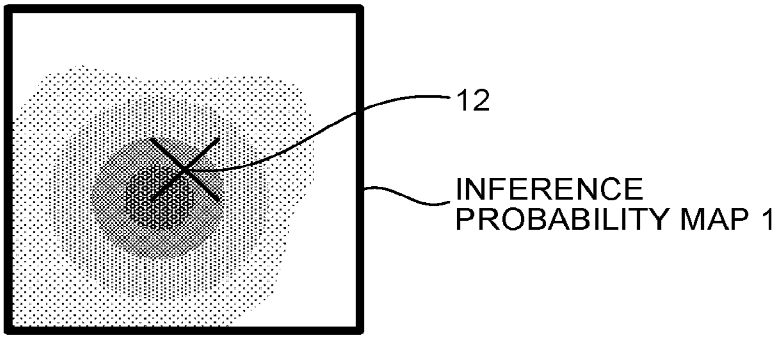
FIG. 7 is a diagram for explaining an example of processing performed by the image processing apparatus according to the first embodiment.
Figure 8:
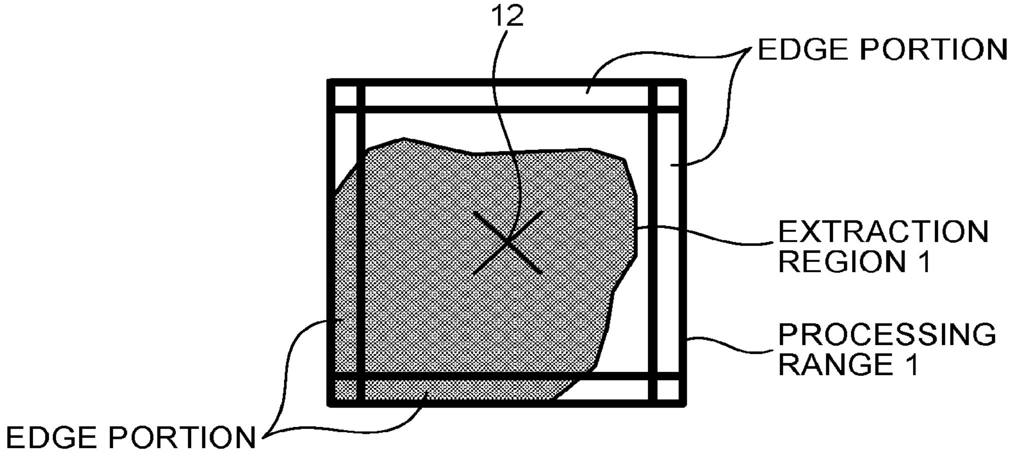
FIG. 8 is a diagram for explaining an example of processing performed by the image processing apparatus according to the first embodiment.

Next, the first extracting function 105*a* sets a value of a probability set to pixels other than the pixel corresponding to the pixel of the extraction region 1 (new extraction region 1) acquired at step S109 out of the entire pixels of the inference probability map 1 extracted at step S103 to “0.0” (step S110). AT step S110, the first extracting function 105*a* does not change the probability set to the pixel corresponding to the pixel of the extraction region 1 acquired at step S109 out of the entire pixels of the inference probability map 1 acquired at step S103. Thus, the first extracting function 105*a* acquires the new inference probability map 1 as illustrated in FIG. 7. When the inference probability map 1 is acquired at step S110, in the processing at step S111 and later, the inference probability map 1 acquired at step S110 is used instead of the inference probability map 1 acquired at step S103. The processing at steps S108 to S110 may be omitted.

Next, the first extracting function 105*a* substitutes the value of the binary threshold $T_1$ used at step S105 into a binary value $T_2$ used at S118 described later as an initial value (step S111). At step S111, the first extracting function 105*a* may substitutes a predetermined initial value “0.5” into the binary threshold 12. The initial value is not limited to “0.5”. Any value may be used as long as it is a value larger than 0.0 and smaller than 1.0.

There is a case in which the extraction region 1 is only a part of the region of interest 11. That is, there is a case in which the first extracting function 105*a* does not extract the entire region of interest 11. Accordingly, as illustrated in FIG. 2B, the determining function 105*c* determines whether the region of interest 11 is present beyond the processing range 1 (step S112).

As a determining method at step S112, for example, two determining methods can be considered. The first determining method will be explained. For example, the determining function 105*c* determines whether the number of pixels present at an either edge portion out of plural edge portions (specifically, six in three dimensions (four in two dimensions)) of the processing range 1 illustrated in FIG. 8 out of pixels in the extraction region 1 is equal to or larger than a predetermined threshold. More specifically, when the number of pixels present at an either edge portion out of plural edge portions out of pixels in the extraction region 1 is equal to or larger than a predetermined threshold, the determining function 105*c* determines that the region of interest 11 is present beyond the processing range 1 in a direction of the relevant edge portion. On the other hand, when the number of pixels present at an edge portion is smaller than the predetermined threshold in all of the edge portions, the determining function 105*c* determines that the region of interest 11 is not present beyond the processing range 1.

The determining function 105*c* may perform, in the first determining method, comparison between a ratio of the number of pixels of the extraction region 1 present at an edge portion to the number of pixels constituting the edge portion and a predetermined threshold, not comparison between the number of pixels and the threshold. Specifically, the determining function 105*c* determines whether the ratio of the number of pixels of the extraction region 1 present at an edge portion to the number of pixels constituting the edge portion, which is either one out of plural edge portions of the processing range 1 is equal to or larger than the predetermined threshold. For example, when the ratio of the number of pixels of the extraction region 1 present at the edge portion to the number of pixels constituting the edge portion, which is either one out of the edge portions, is equal to or larger than the predetermined threshold, the determining function 105*c* determines that the region of interest 11 is present beyond the processing range 1 in the direction of the relevant edge portion. On the other hand, when the ratio of the number of pixels of the extraction region 1 present at the edge portion to the number of pixels constituting the edge portion is smaller than the predetermined threshold in all of the edge portions, the determining function 105*c* determines that the region of interest 11 is not present beyond the processing range 1.

The edge portions are explained. In the present embodiment, there are six edge portions in three dimensions as described above. Various definitions can be considered for edge portion. The first definition of edge portion will be explained. For example, in the first definition of edge portion, respective regions of six edge portions are regions including only all pixels in contact with six planes of a cube defining the processing range 1 out or pixels in the processing range 1.

The second definition of edge portion will be explained. For example, in the second definition of edge portion, respective regions of six edge portions are regions including only all pixels that are present within a predetermined distance from respective six planes of a cube defining the processing range 1 out of pixels in the processing range 1.

The third definition of edge portion will be explained. For example, in the third definition of edge portion, respective regions of six edge portions are regions including only all pixels that are present at a position distant for a predetermined distance along respective directions of an X axis, a Y axis, and a Z axis from the center of the processing range 1 out of pixels in the processing range 1.

When the first determining method is used, and a first rule is adopted at step S114 described later, the direction acquiring function 105*d* acquires information indicating in which direction an edge portion is present in which the number of pixels included in the extraction region 1 in the edge portion is equal to or larger than a predetermined threshold. Alternatively, the direction acquiring function 105*d* acquires information indicating in which direction the edge portion is present in which the ratio described above is equal to or larger than a predetermined threshold. That is, the direction acquiring function 105*d* acquires information relating to a direction in which the region of interest 11 extends therebeyond.

Next, the second determining method will be explained. For example, the determining function 105*c* determines whether a statistical amount (statistical value) of plural probabilities set to pixels present at either edge portion out of plural edge portions of the processing range 1 out of pixels of the inference probability map 1 is equal to or larger than a predetermined threshold. The statistical amount of probabilities is, for example, a sum, an average, a variance, or the like of plural probabilities. More specifically, when the statistical amount of probabilities set to pixels present at either edge portion out of plural edge portions out of pixels of the inference probability map 1 is equal to or larger than a predetermined threshold, the determining function 105*c* determines that the region of interest 11 is present beyond the processing range 1 in the direction of the relevant edge portion. On the other hand, when the statistical amount of probabilities set to pixels is smaller than the predetermined threshold in all of edge portions, the determining function 105*c* determines that the region of interest 11 is not present beyond the processing range 1.

When the second determining method is used, and the first rule is adopted at step S114 described above, the direction acquiring function 105*d* acquires information indicating in which direction the edge portion is present in which the statistical amount of probabilities set to pixels included in the inference probability map 1 in the edge portion is equal to or larger than a predetermined threshold. That is, the direction acquiring function 105*d* acquires information relating to in which direction the region of interest 11 extends therebeyond.

As described above, the determining function 105*c* determines whether the extraction region 1 is a part of the region of interest by determining whether at least a part of the extraction region 1 is present at an edge portion of the processing range 1. Moreover, the determining function 105*c* determines whether the extraction region 1 is a part of the region of interest 11 by determining whether a statistical amount of probabilities of the inference probability map 1 present at an edge portion of the processing range 1 is equal to or larger than a predetermined threshold.

Moreover, the direction acquiring function 105*d* acquires a direction in which a processing range 2 described later is set based on the processing range 1 when the determining function 105*c* determines that the extraction region 1 is a part of the region of interest 11. The processing range 2 is an example of a second processing range. Furthermore, the direction acquiring function 105*d* acquires a direction in which the extraction region 1 is determined as a part of the region of interest 11 as a direction in which the processing range 2 is set based on the processing range 1, based on a direction in which relative to the center of the processing range 1 the extraction region 1 is determined as a part of the region of interest 11.

When the region of interest 11 is not present beyond the processing range 1 (step S112: NO), the first extracting function 105*a* determines the extraction region 1 as a final extraction region (step S113), and ends the region extraction processing.

In the present embodiment, the image processing apparatus 100 outputs the final extraction region. Specifically, the display control function 105*g* controls the display 104 to display the final extraction region. Thus, a user, such as a doctor, can see the extraction region displayed on the display 104 as the region of interest 11. The display control function 105*g* may superimpose the final extraction region on medical image data, and may control the display 104 such that a medical image on which the final extraction region is superimposed. In this case, the display control function 105*g* may superimpose the final extraction region as a semitransparent color image, or may superimpose as a shape such as a boundary line. Thus, the user can grasp in which position on the medical image the region of interest 11 is present by viewing the extraction region positioned on a medical image.

On the other hand, when the region of interest 11 is present beyond the processing range 1 (step S112: YES), the second extracting function 105*e* acquires a list of at least one of the processing range 2 based on a predetermined rule, and acquires partial image data 2 in the respective processing range 2 from the medical image data, to thereby acquire a list of the partial image data 2 (step S114). The list of the processing range 2 is information in which coordinates of at least one processing range 2 are registered. Moreover, the list of the partial image data 2 is, for example, a collection of the partial image data 2.

As a rule when the list of the processing range 2 is to be acquired, for example, either one of a first rule and a second rule is adopted. That is, the second extracting function 105*e* acquires a list of the processing range 2 based on either one rule out of two rules.

Figure 9:
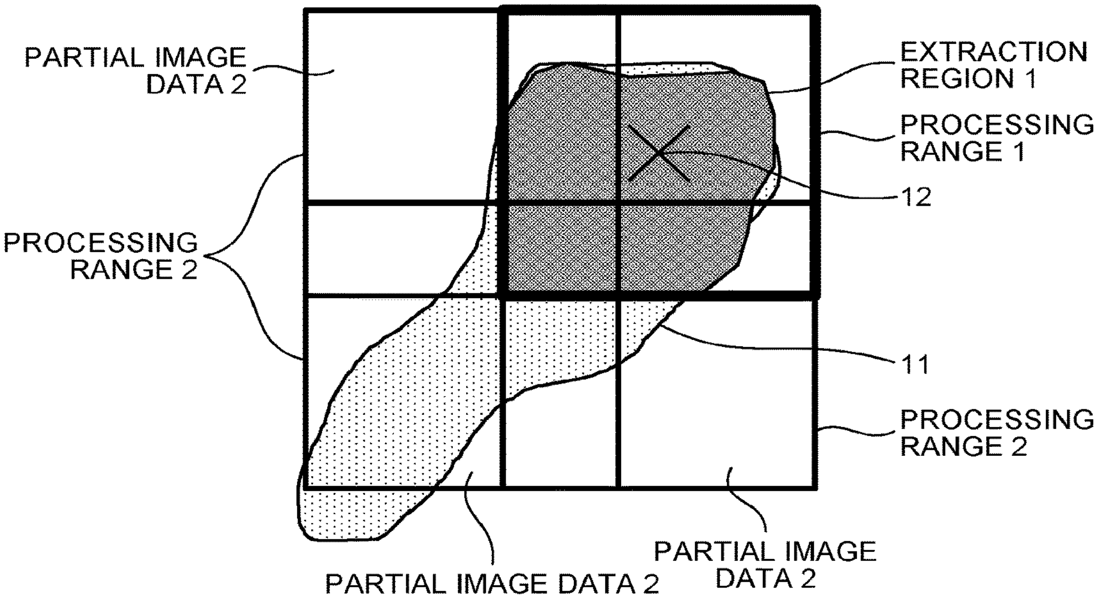
FIG. 9 is a diagram for explaining an example of processing performed by the image processing apparatus according to the first embodiment.

First, the first rule will be explained. In the first rule, a list of the processing range 2 illustrated in FIG. 9 is acquired based on information indicating in which direction the region of interest 11 extends therebeyond.

Specifically, in the first rule, coordinates of a position that is shifted by predetermined length $L_1$ toward all of directions in which the region of interest 11 is determined to extend therebeyond from a position of the processing range 1 are acquired, as coordinates of the processing range 2. For example, a case in which directions in which the region of interest 11 extends therebeyond are three directions of a minus direction (negative direction) of the X axis, a plus direction (positive direction) of the Y axis, and a plus direction of the Z axis will be explained. In this case, the second extracting function 105*e* acquires seven coordinates of the processing range 2 that are shifted by $(-L_1, 0, 0)$, $(-L_1, +L_1, 0)$ $(0, +L_1, 0)$ $(0, 0, +L_1)$, $(-L_1, 0, +L_1)$, $(-L_1, +L_1, +L_1)$, $(0, +L_1, +L_1)$ in the respective directions of (X, Y, Z) from the position of the processing range 1 based on the first rule.

The length $L_1$ is a length at a predetermined magnification (for example, 1×, ⅘×, ⅔×, ½×, or the like) of a length of one side of the processing range 1. When the predetermined magnification is 1×, the processing range 1 and the processing range 2 are in contact with each other, and there is no overlapping portions between the processing range 1 and the processing range 2. On the other hand, when the predetermined magnification is smaller than 1×, there is an overlapping portion between the processing range 1 and the processing range 2.

An advantage of the first rule is that processing time can be suppressed because the number of the processing range 2 can be reduced. When the shape of the region of interest 11 is estimated to be in a generally convex shape such as an ellipsoid, the first rule in which the processing range 2 is expanded in only a limited direction is preferable to be used.

Figure 10:
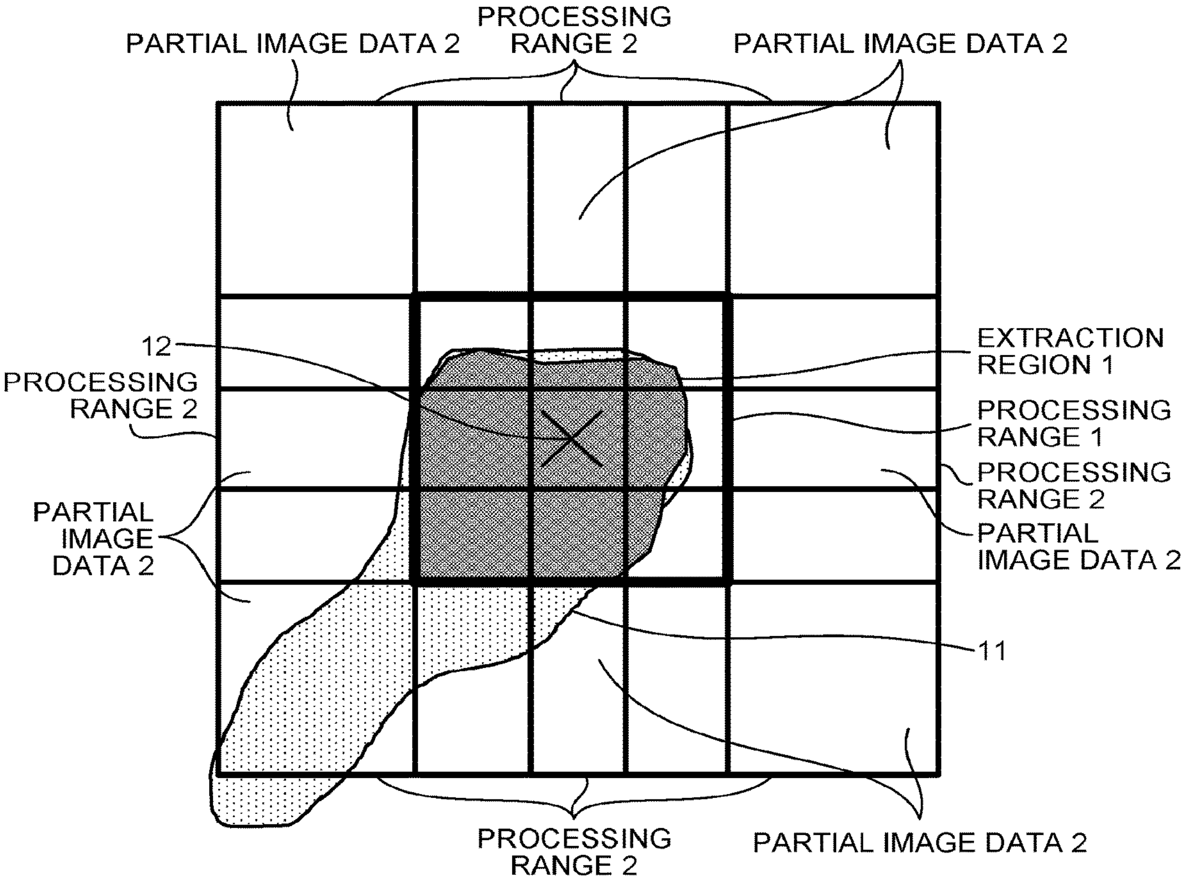
FIG. 10 is a diagram for explaining an example of processing performed by the image processing apparatus according to the first embodiment.

Next, the second rule will be explained. In the second rule, a list of the processing range 2 illustrated in FIG. 10 is acquired based on a determination result that the region of interest 11 is present beyond the processing range 1 at step S112. That is, in the second rule, a list of the processing range 2 is acquired without considering a direction in which the region of interest 11 extends therebeyond.

Specifically, in the second rule, coordinates of positions that are shifted by the predetermined length $L_1$ in a plus direction or a minus direction along at least one axis of the X axis, the Y axis, and the Z axis from the position of the processing range 1, as coordinates of the position of the processing range 2. For example, the second extracting function 105*e* acquires 26 coordinates of the processing range 2 based on the second rule.

An advantage of the second rule is that a risk of not extracting a part of the region of interest 11 can be reduced because the processing range 2 is expanded in all directions. When it is estimated that the shape of the region of interest 11 is significantly complicated, it is preferable to use the second rule in which the processing range 2 is expanded in all directions.

Next, the second extracting function 105*e* acquires a list of an inference probability map 2 by acquiring the inference probability map 2 corresponding to the respective partial image data 2 included in the list of the partial image data 2, by using the inference model (S115). The list of the inference probability map 2 is a collection of the inference probability map 2.

An example of processing at step S115 will be explained. The inference model is stored in the storage circuit 102, and when the partial image data 2 in a predetermined fixed size (fixed size 1) is input, the inference probability map 2 that is a map indicating a probability that respective pixels included in the partial image data 2 are a pixel included in the region of interest 11 is output. The probability is a value from 0.0 to 1.0. The inference model used at step S103 and the inference model used at step S115 may be the same neural network, or may be different neural networks. When the inference model used at step S103 and the inference model used at step S115 are different, the inference models as a region extraction means for which an optimal training has been performed at respective steps are used.

At step S115, the second extracting function 105*e* acquires an inference model stored in the storage circuit 102. The second extracting function 105*e* inputs the partial image data 2 to the acquired inference model, and acquires the inference probability map 2 output from the inference model.

At step S115, the second extracting function 105*e* may resize the partial image data 2 to make pixel spacing of the partial image data 2 be lxlxl [mm], and may input the isotropically rescaled image data obtained as a result of resizing to the inference model. In this case, the coordinates of the specified point 12 are converted into coordinates corresponding to the isotropic image data.

As described above, the second extracting function 105*e* extracts inference probability map 2 that is acquired by calculating a probability that respective pixels of the partial image data 2 are a pixel included in the region of interest 11.

Next, the integrating function 105*f* integrates the inference probability map 1 and all of the inference probability maps 2 included in the list of the inference probability map 2 acquired at step S115 such that positions thereof are aligned with each other based on the respective coordinates, and thereby acquires the new inference probability map 1 (step S116).

At step S116, a method of integrating the inference probability map 1 and all of the inference probability maps 2 included in the list of the inference probability map 2 may be any method. In the following, three specific examples are explained.

In a first example, when at least two inference probability maps have overlapping pixel positions out of all of the inference probability maps out of the inference probability map 1 and all of the inference probability maps 2 included in the list of the inference probability map 2, the integrating function 105*f* regards the highest probability out of plural probabilities at the overlapping pixel positions as the probability of the new inference probability map 1. As described, in the first example, when there is an overlapping region in the inference probability map 1 and the inference probability map 2, the integrating function 105*f* acquires the new inference probability map 1 by using a higher probability out of a probability of each pixel in the overlapping region of the inference probability map 1 and a probability of each pixel in the overlapping region of the inference probability map 2, as the probability of each pixel of a region corresponding to the overlapping region in the new inference probability map 1.

In the second example, when there is an overlapping pixel position in at least two inference probability maps out of all of the inference probability maps of the inference probability map 1 and all of the inference probability maps 2 included in the list of the inference probability map 2, the integrating function **105*f* uses an average value of plural probabilities at the overlapping pixel position as the probability of the new inference probability map 1. As described, in the second example, for example, when there is an overlapping region in the inference probability map 1 and the inference probability map 2, the integrating function 105*f* acquires the new inference probability map 1 by using an average value of a probability of each pixel in the overlapping region of the inference probability map 1 and a probability of each pixel in the overlapping region of the new inference probability map 2, as the probability of each pixel of a region corresponding to the overlapping region in the new inference probability map 1**.

In the third example, when there is an overlapping pixel position in at least two inference probability maps out of all of inference probability maps of the first inference probability map 1 and all of the inference probability maps 2 included in the list of the inference probability map 2, the integrating function **105*f* uses a value obtained by weighting respective probabilities according to a distance from the center of a processing range to which each pixel belongs, and by summing them up as a probability in the new inference probability map 1 at an overlapping pixel position. There is a tendency that the accuracy of a probability is high at the center of the processing range, and the accuracy of a probability becomes lower as it departs farther from the center of the processing range. Therefore, the integrating function 105*f* multiplies a probability by a weight that increases as it gets closer to the center of the processing range and decreases as it departs farther from the center of the processing range, and uses a sum of plural probabilities (for example, two probabilities) multiplied by the weight as the probability of the new inference probability map 1. Thus, the inference probability map 1** in which a highly accurate probability is set can be acquired.

As described, in the third example, when there is an overlapping region in the inference probability map 1 and the inference probability map 2, the integrating function **105*f* calculates a probability of each pixel of a region corresponding to an overlapping region in the new inference probability map 1 by summing up a first value that is obtained by multiplying a probability of each pixel in the overlapping region of the inference probability map 1 by a weight that decreases as it departs farther from the center of the processing range 1 and a second value that is obtained by multiplying a probability of each pixel in the overlapping region of the inference probability map 2 by the weight that decreases as it departs farther from the center of the processing range 2**.

Figure 11:
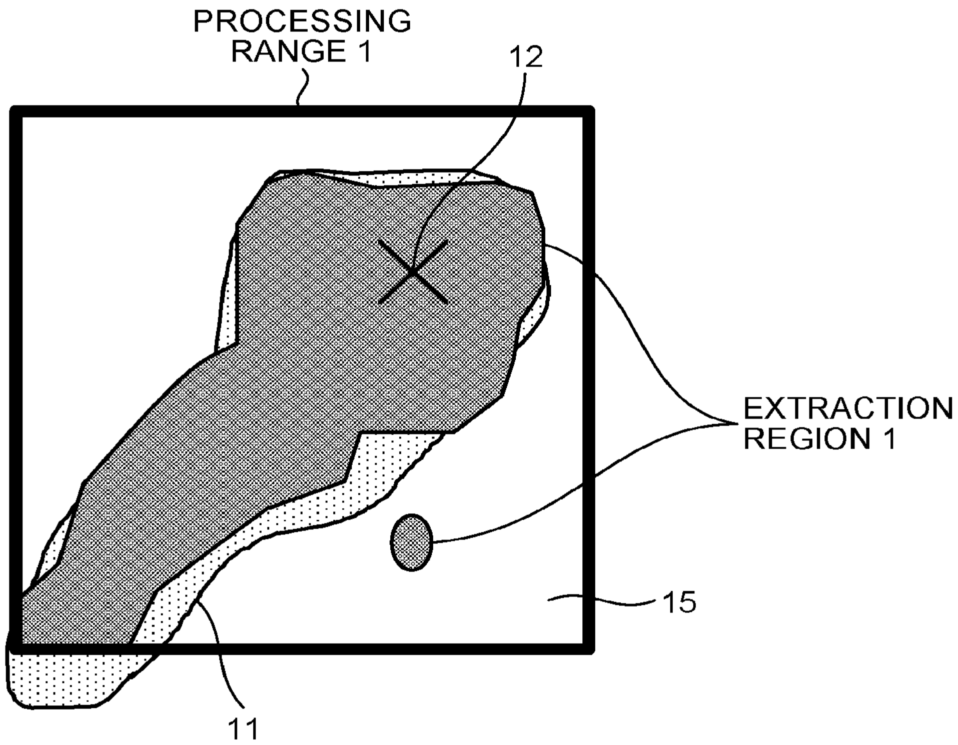
FIG. 11 is a diagram for explaining an example of processing performed by the image processing apparatus according to the first embodiment.

Next, the integrating function **105*f* integrates the processing range and all of the processing ranges 2 included in the list of the processing range 2, to acquire the new processing range 1 (step S117). For example, the integrating function 105*f* acquires the new processing range 1 as illustrated in FIG. 11 by integrating the processing range 1 and all of the processing ranges 2 illustrated in FIG. 9 or FIG. 10** such that positions thereof are aligned with each other.

Next, the integrating function **105*f* acquires the new extraction region 1 by performing binary processing with respect to the inference probability map 1 acquired at step S116 using the binary threshold 12 (step S118**).

An example of the processing at step S118 will be explained. At step S118, the integrating function **105*f* acquires three-dimensional binary image data 15 illustrated in FIG. 11 by performing binary processing with respect to the inference probability map 1 using the binary threshold $T_2$. That is, in the inference probability map 1, a value indicating the inside of the extraction region 1 (value corresponding to black in the example of FIG. 11) is set to a pixel of the binary image data 15 corresponding to a pixel to which a value equal to or larger than the binary threshold $T_2$ is set. Moreover, in the inference probability map 1, a value indicating the outside of the extraction region 1 (value corresponding to white in the example of FIG. 11) is set to a pixel of the binary image data 15 corresponding to a pixel to which a value smaller than the binary threshold $T_2$ is set. As illustrated in FIG. 11, out of all pixels in the binary image data 15, the integrating function 105*f* extracts a region constituted of pixels to which the value indicating the inside of the extraction region as the new extraction region 1. In the example of FIG. 11, a case in which the integrating function 105*f* extracts the extraction region 1 including two partial regions from the binary image data 15** is illustrated.

In the new extraction region 1 acquired at step S118, the extraction region that is acquired from the partial image data 2 included in the list of the partial image data 2 acquired at step S114 is included. the extraction region acquired from the partial image data 2 is denoted as "extraction region 2". This extraction region 2 is acquired by the second extracting function **105*e* and the integrating function 105*f*. That is, the second extracting function 105*e* acquires the inference probability map 2 that is acquired by calculating a probability that respective pixels of the partial image data 2 are pixels included in the region of interest 11. The integrating function 105*f* extracts the extraction region 2 by binarizing the inference probability map 2. Specifically, the integrating function 105*f* extracts a region constituted of pixels to which the value indicating the inside of the extraction region 1 out of all pixels in the binary image data 15 acquired by binarizing the inference probability map 2, as the extraction region 2. That is, when the extraction region 1 extracted in the partial image data 1 is regarded as a part of the region of interest 11, the second extracting function 105*e* and the integrating function 105*f* extract the extraction region 2 that is estimated as the region of interest 11 from the partial image data 2 included in the processing range 2 that is in contact with the edge portion of the processing range 1 or that includes at least a part of the edge portion from medical image data. The partial image data 2 is one example of second partial image data. The inference probability map 2 is one example of a second inference probability map. The extraction region 2** is one example of a second extraction region.

Moreover, as described above, the second extracting function **105*e* sets the processing range 2 at a position shifted from the processing range 1 in a direction acquired by the direction acquiring function 105*d* by a predetermined distance. Alternatively, the second extracting function 105*e* sets the processing range 2 at a position respectively shifted from the processing range 1 in all directions in which the edge portions of the processing range 1 are present by a predetermined distance. The integrating function 105*f* then extracts the extraction region 2 from the partial image data 2 included in the set processing range 2**.

Next, the removing function **105*b* determines whether the extraction region 1 acquired at step S118** includes plural partial regions that are not connected to each other (step S119). For example, in the case illustrated in FIG. 11, the removing function 105*b* determines that the extraction region 1 includes two partial regions that are not connected to each other (step S119: YES).

When the extraction region 1 does not include plural partial regions that are not connected to each other (step S119: NO), that is, when the extraction region 1 is a single region, the removing function 105*b* proceeds to step S122.

On the other hand, when the extraction region 1 includes plural partial regions that are not connected to each other (step S119: YES), the removing function 105*b* leaves only a specific partial region out of the plural partial regions, and removes the other partial regions (step S120). At step S120, for example, the removing function 105*b* performs processing similar to the processing at step S109.

Figure 12:
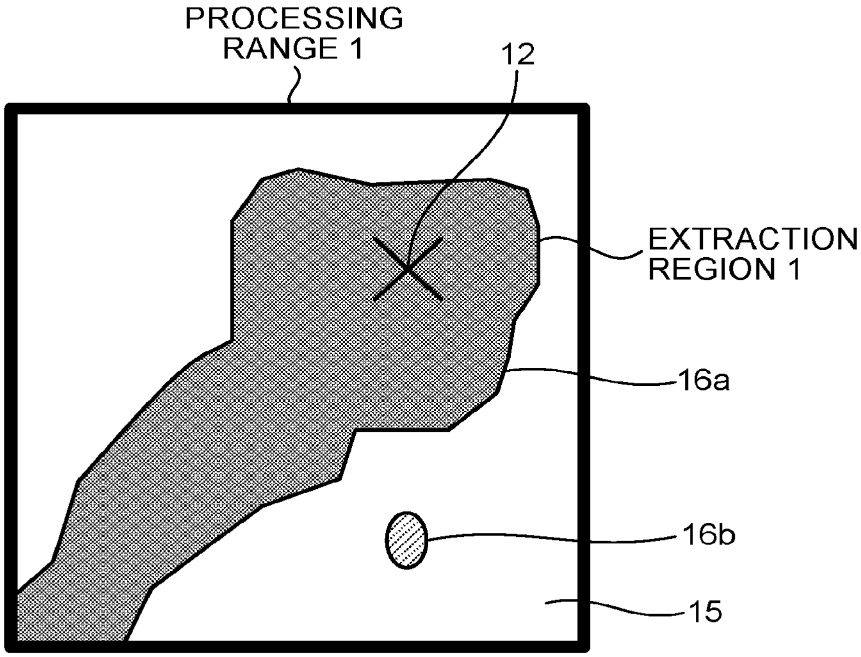
FIG. 12 is a diagram for explaining an example of processing performed by the image processing apparatus according to the first embodiment.

As illustrated in FIG. 12, at step S120, the removing function 105*b* leaves only a partial region 16*a* that includes the specified point 12 out of partial regions 16*a* and 16*b*, and removes the other partial region 16*b*. Thus, the removing function 105*b* acquires the partial region 16*a* as the new extraction region 1.

By the processing at step S120, it is possible to remove an unnecessary partial region that has a high possibility of erroneous extraction of extracting a region that is not the region of interest 11 by mistake. Moreover, as a result of removing the unnecessary partial region having a high possibility of erroneous extraction, it is possible to suppress increase of computational time because of an increased processing range based on the region erroneously extracted.

Figure 13:
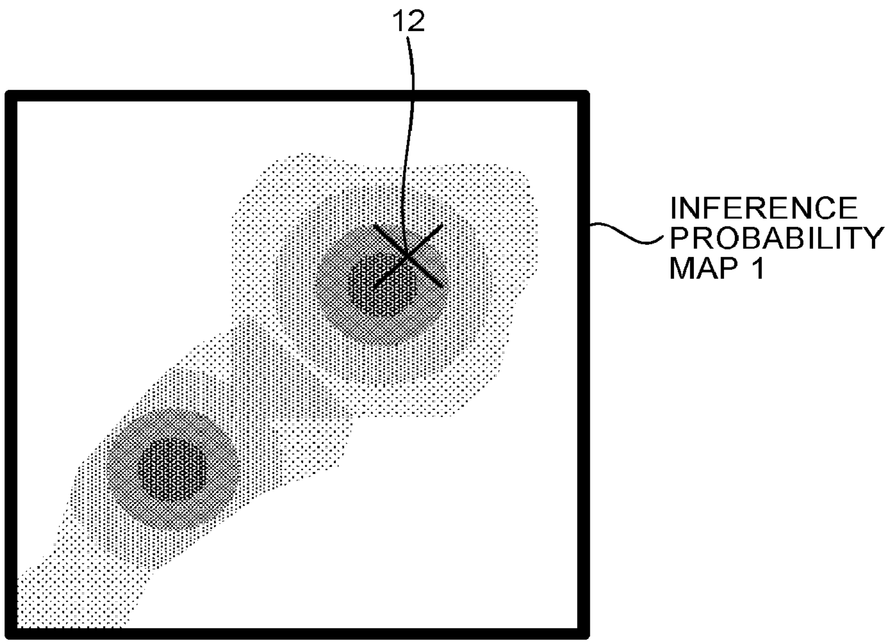
FIG. 13 is a diagram for explaining an example of processing performed by the image processing apparatus according to the first embodiment.

Next, the integrating function 105*f* sets a value of a probability set to a pixel other than a pixel corresponding to pixels of the extraction region 1 (new extraction region 1) that is acquired at step S120 out of all of pixels in the inference probability map 1 acquired at step S116 to "0.0" (step S121). At step S121, the integrating function 105*f* does not change the probability set to a pixel corresponding to pixels of the extraction region 1 acquired at step S120 out of all of pixels in the inference probability map 1 acquired at step S116. Thus, the integrating function 105*f* acquires the new inference probability map 1 as illustrated in FIG. 13. When the inference probability map 1 is acquired at step S121, in processing at step S122 and later, the inference probability map 1 that is acquired at step S121 is used instead of the inference probability map 1 acquired at step S116. The processing at steps S119 to S121 may be omitted.

Next, the integrating function 105*f* increases the binary threshold $T_2$ in accordance with a predetermined rule (step S122). The predetermined rule is, for example, a rule that "0.2" is added to a value of the binary threshold $T_2$. There is a tendency of extracting a region that is not the region of interest 11 by mistake as the processing range 2 departs farther from the specified point 12. Accordingly, by the processing at step S122, it is possible to suppress extraction of a region by mistake at a position away from the specified point 12.

The integrating function 105*f* then returns to step S112. When the binary threshold $T_2$ that has increased at step S122 becomes larger than a predetermined maximum threshold (for example, 0.9 or 1.0), the integrating function 105*f* sets the maximum threshold to the binary threshold $T_2$, and returns to step S122. The processing at step S112 may be omitted.

As it returns to step S112, while it is determined that the region of interest 11 is present beyond the extraction region 1, the processing at step S112 to S122 is repeatedly performed. That is, the processing range 1 is repeatedly expanded.

As described above, the integrating function 105*f* increases the binary threshold $T_2$ used when the inference probability map 2 is binarized in accordance with a predetermined rule to make it larger than the binary threshold $T_1$ used when the inference probability map 1 is binarized. At step S118, the integrating function 105*f* binarizes the inference probability map 2 included in the new inference probability map 1 using the increased binary threshold $T_2$, and thereby extracts the extraction region 2 included in the new extraction region 1.

Moreover, the integrating function 105*f* integrates the extraction region 1 and the extraction region 2, to acquire a new extraction region.

As above, the image processing apparatus 100 according to the first embodiment has been explained. According to the first embodiment, when the region of interest 11 is larger than the processing range 1, by repeating respective processing of the processing at step S112 to processing at step S122 for the necessary number of times, the processing range 1 is repeatedly expanded. Therefore, the region of interest 11 in various sizes can be extracted with high accuracy.

Moreover, the expansion of the processing range 1 is stopped at step S113. Therefore, compared to the conventional technique in which an entire image is processed by dividing into a grid, the number of processing can be suppressed, and it is possible to process more speedily.

Therefore, according to the image processing apparatus 100 according to the first embodiment, the region of interest 11 captured in medical image data can be extracted highly accurately and at high speed.

First Modification of First Embodiment

Next, the image processing apparatus 100 according to a first modification of the first embodiment will be explained. In the following explanation, a configuration different between the first embodiment and the first modification of the first embodiment will be mainly explained, and explanation of an identical or similar configuration may be omitted. Furthermore, in the following explanation, identical signs are assigned to configurations identical or similar to those of the first embodiment, and explanation thereof may be omitted.

Figure 14:
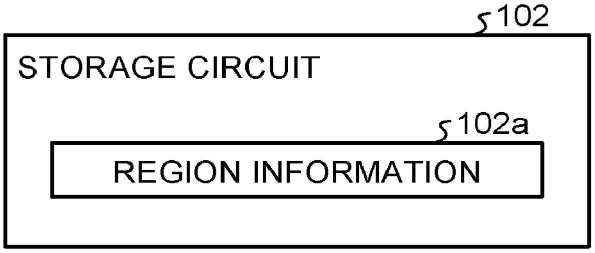
FIG. 14 is a diagram for explaining an example of processing performed by the image processing apparatus according to a first modification of the first embodiment.

FIG. 14 is a diagram for explaining about an example of processing performed by the image processing apparatus 100 according to the first modification of the first embodiment. In the first modification of the first embodiment, for example, as illustrated in FIG. 14, region information 102*a* indicating at least one of a region of a body part or an organ in which the region of interest 11 is present and a region of a body part or an organ in which the region of interest 11 is not present is stored in the storage circuit 102. For example, the region of interest 11 is a pulmonary nodule, the pulmonary nodule is present in a pulmonary field. Therefore, at step S114, the second extracting function 105*e* extracts the pulmonary field from medical image data. The second extracting function 105*e* stores the region information 102*a* indicating the extracted pulmonary field in the storage circuit 102.

At step S114, the second extracting function 105*e* acquires the region information 102*a* from the storage circuit 102. At step S114, when acquiring a list of coordinates of the processing range 2, the second extracting function 105*e* acquires coordinates that are included only in the pulmonary field indicated by the region information 102*a* from among coordinates of the processing ranges 2 that are acquired based on the first rule or the second rule as coordinates of the processing range 2. That is, out of coordinates of the processing ranges 2 that are acquired based on the first rule and the second rule, coordinates included only in the pulmonary field indicated by the region information 102*a* are to be included in the list of coordinates of the processing range 2. In other words, out of coordinates of the processing ranges 2 that are acquired based on the first rule and the second rule, coordinates included in a region other than the pulmonary field indicated by the region information 102*a* are not included in the list of coordinates of the processing range 2.

Moreover, for example, when the region of interest 11 is a tumor metastasized to a lymph node, the tumor is present in a trunk region, and is not present in a bone region. Therefore, at step S114, the second extracting function 105*e* extracts the trunk region and the bone region from the medical image data. The second extracting function 105*e* stores the region information 102*a* indicating the extracted trunk region and bone region in the storage circuit 102.

At step S114, the second extracting function 105*e* acquires the region information 102*a* from the storage circuit 102. When acquiring the list of coordinates of the processing range 2 at step S114, the second extracting function 105*e* acquires coordinates included in the trunk region indicated by the region information 102*a* and the included in a region outside the bone region indicated by the region information 102*a* from among coordinates of the processing ranges 2 that are acquired based on the first rule or the second rule as coordinates of the processing range 2. That is, out of coordinates of the processing ranges 2 that are acquired based on the first rule and the second rule, coordinates included in the trunk region indicated by the region information 102*a* and included in the region outside the bone region are to be included in the list of coordinates of the processing range 2. In other words, out of coordinates of the processing ranges 2 that are acquired based on the first rule and the second rule, coordinates included in the trunk region indicated by the region information 102*a* and not included in the region outside the bone region are not included in the list of coordinates of the processing range 2.

Accordingly, in the first modification of the first embodiment, the second extracting function 105*e* sets the processing range 2 using the region information 102*a* indicating at least one of the region in which the region of interest 11 is present and the region in which the region of interest 11 is not present, and extracts the extraction region 2 that is estimated as the region of interest 11 from the partial image data included in the set processing range 2.

According to the image processing apparatus 100 according to the first modification of the first embodiment, it is possible to reduce erroneous extraction of the region of interest 11 in a region in which the region of interest 11 is not present. Moreover, because a range in which the processing range 2 is to be set is limited, the processing time can be reduced.

Second Modification of First Embodiment

Next, the image processing apparatus 100 according to a second modification of the first embodiment will be explained. In the following explanation, a configuration different between the first embodiment and the second modification of the first embodiment will be mainly explained, and explanation of an identical or similar configuration may be omitted. Furthermore, in the following explanation, identical signs are assigned to configurations identical or similar to those of the first embodiment, and explanation thereof may be omitted.

In the first embodiment, a case in which the extraction region 1 is regarded as the final extraction region at step S113 has been explained. On the other hand, in the present modification, the inference probability map 1 is to be the final extraction region. The present modification will be specifically explained. In the present modification, when it is determined that the region of interest 11 does not extend beyond the processing range 1 at step S112 (step S112: NO), the new inference probability map 1 that is acquired at latest step S116 is regarded as the final extraction region at step S113. The new inference probability map 1 is displayed on the display 104. When the processing at step S116 is not performed and the new inference probability map 1 is acquired at step S110, this inference probability map 1 is regarded as the final extraction region, and is displayed on the display 104. Moreover, when the processing at step S116 and the processing at step S110 are not performed, the inference probability map 1 acquired at step S103 is regarded as the final extraction region, and is displayed on the display 104.

The new inference probability map 1 acquired at step S116 is an inference probability map that is obtained by integrating the inference probability map 1 acquired at step S103 or S110 and at least one of the inference probability map 2 included in the list of the inference probability map 2 acquired at step S115.

Therefore, in the present modification, the inference probability map 1 acquired at step S103 or S110 and at least one of the inference probability map 2 included in the list of the inference probability map 2 acquired at step S115 are included in the final extraction region. That is, in the present modification, the first extracting function 105*a* extracts the inference probability map 1 acquired at step S103 or S110 as a part of the final extraction region. Moreover, in the present modification, the integrating function 105*f* extracts at least one of the inference probability map 2 included in the list of the inference probability map 2 acquired at step S115 as a part of the final extraction region. At step S113, the display control function 105*g* controls the display 104 to display the new inference probability map 1 that includes the inference probability map 1 acquired at step S103 or S110 and at least one of the inference probability map 2 included in the list of the inference probability map 2 acquired at step S115.

As above, the image processing apparatus 100 according to the second modification of the first embodiment has been explained. According to the image processing apparatus 100 according to the second modification of the first embodiment, a user can view the new inference probability map 1.

Second Embodiment

Next, the image processing apparatus 100 according to a second embodiment will be explained. In the following explanation, a configuration different between the first embodiment and the second embodiment will be mainly explained, and explanation of an identical or similar configuration may be omitted. Furthermore, in the following explanation, identical signs are assigned to configurations identical or similar to those of the first embodiment, and explanation thereof may be omitted.

Figure 15:
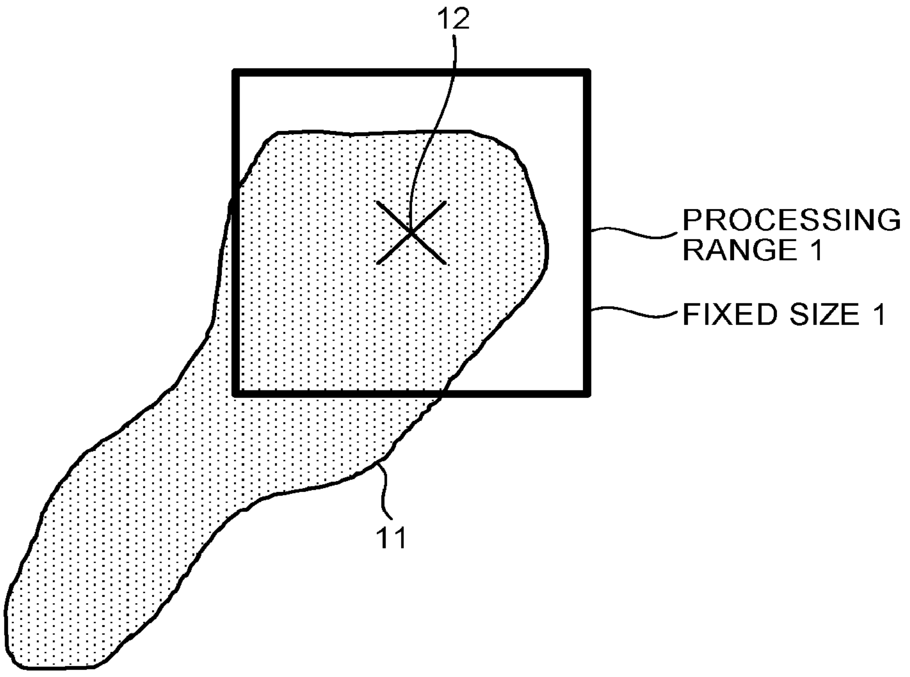
FIG. 15 is a diagram illustrating an example of a fixed size 1 used in the first embodiment.

FIG. 15 is a diagram illustrating an example of the fixed size 1 used in the first embodiment previously explained.

Figure 16:
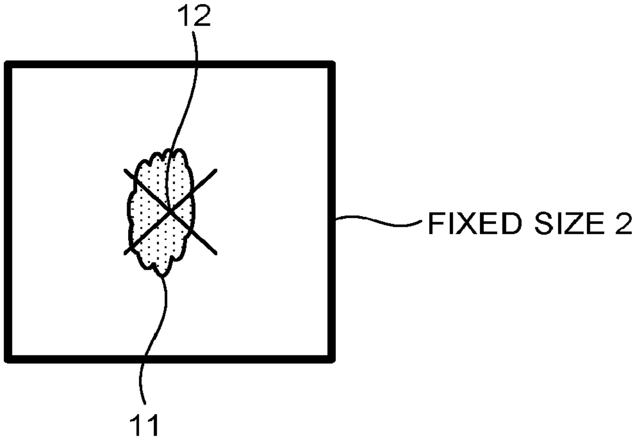
FIG. 16 is a diagram illustrating an example of a fixed size 2 used in the second embodiment.

FIG. 16 is a diagram illustrating an example of a fixed size 2 that is used in the second embodiment.

An inference model (trained model, neural network) used at step S103 of the first embodiment has been trained by using training data of a predetermined fixed size (fixed size 1). For example, the fixed size 1 illustrated in FIG. 15 is a size larger than the size of the general region of interest 11. This is because, if it is set to be large, the number of times the processing range 1 to be expanded can be reduced for the region of interest 11 in a large size, and computational time can be thereby suppressed.

However, when the size of the region of interest 11 is significantly smaller than the fixed size 1, the extraction accuracy of a region becomes higher if a region extraction means (inference model, trained model, neural network) that has been trained using a fixed size (fixed size 2 illustrated in FIG. 16) smaller than the fixed size 1 is used.

Accordingly, in the second embodiment, when the region of interest 11 is estimated (inferred) to be smaller than the fixed size 2, to improve the extraction accuracy of a region, the image processing apparatus 100 performs processing explained below.

Figure 17A:
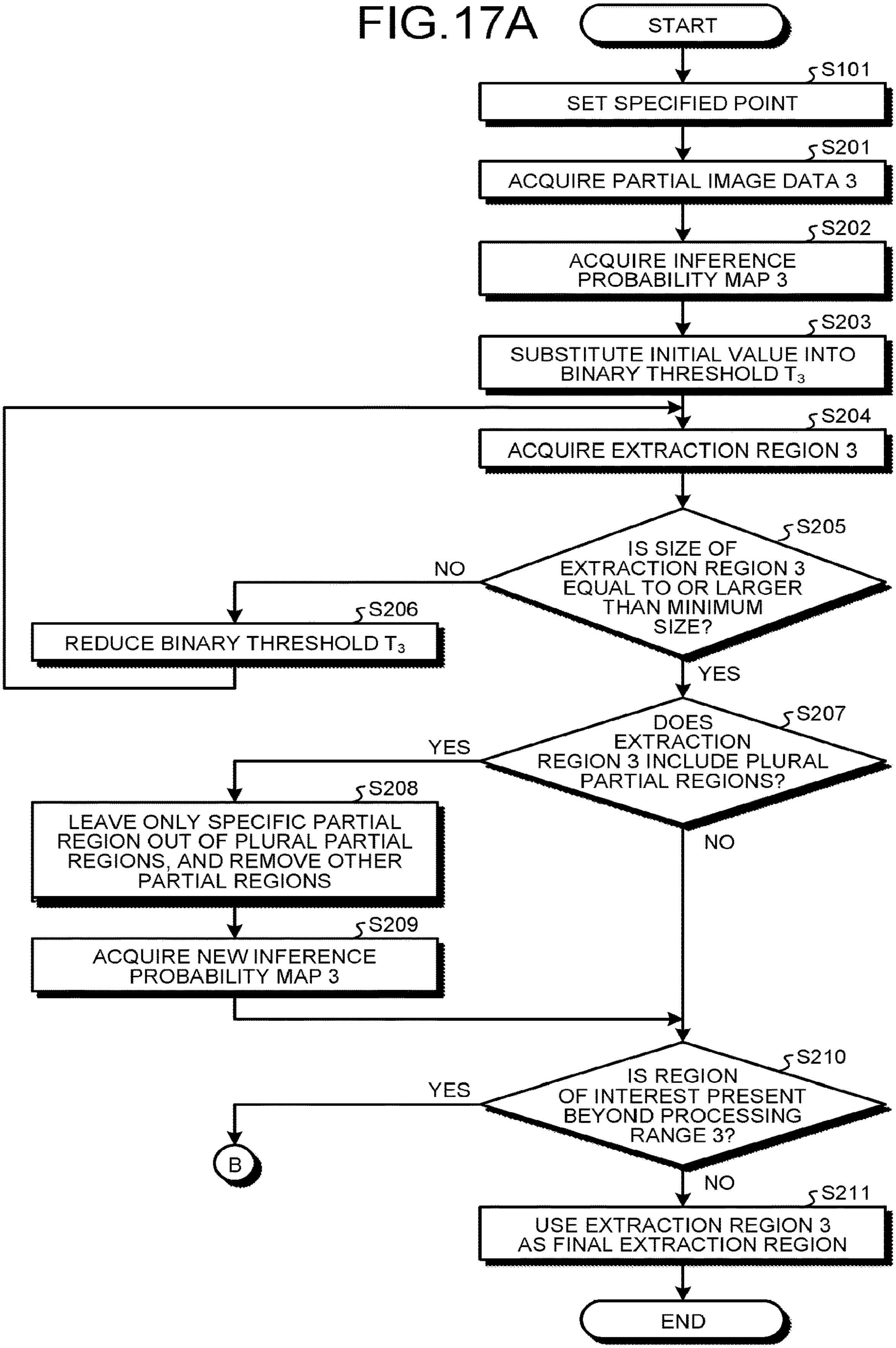
FIG. 17A is a flowchart illustrating a flow of an example of region extraction processing performed by an image processing apparatus according to the second embodiment.
Figure 17B:
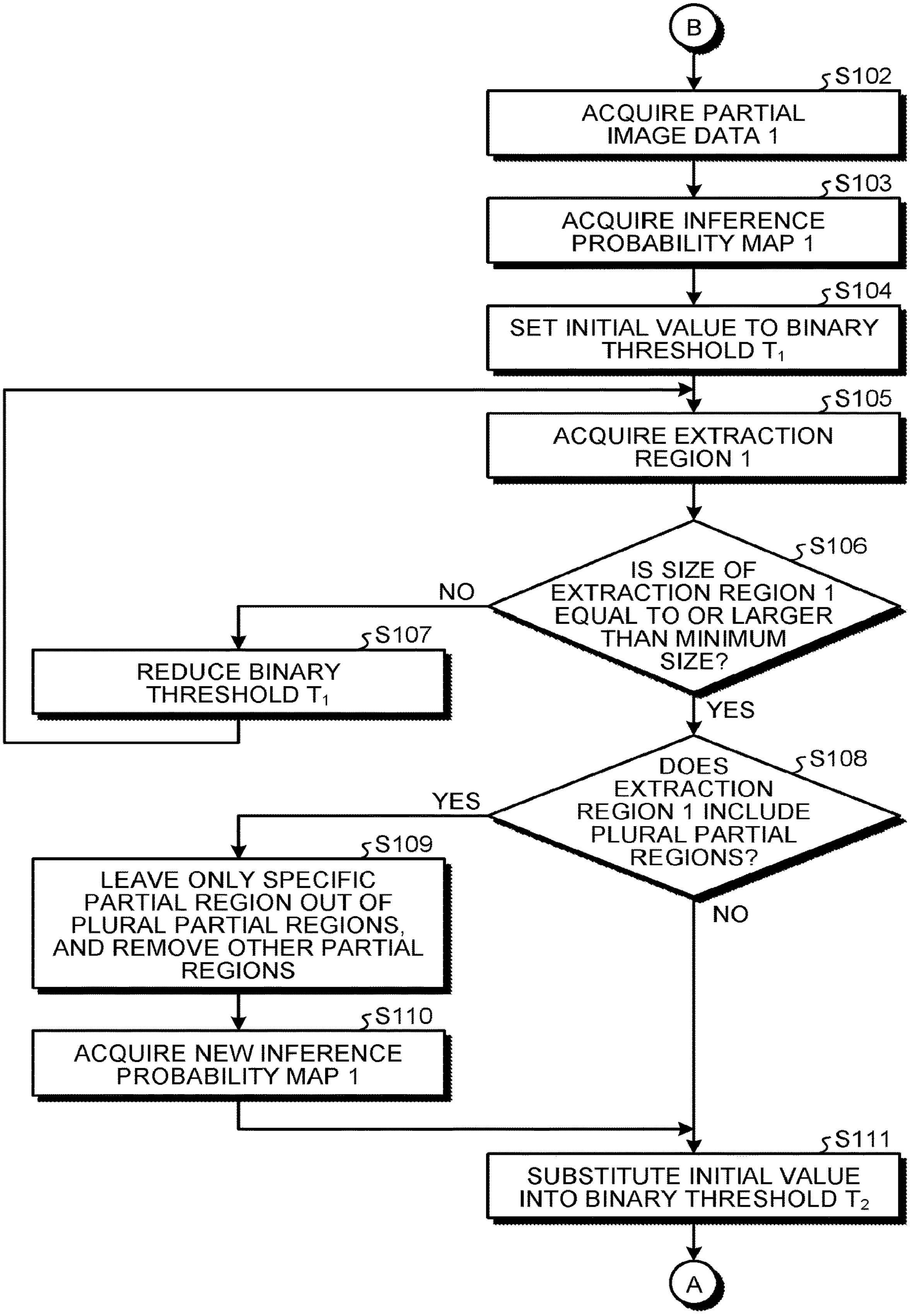
FIG. 17B is a flowchart illustrating a flow of an example of the region extraction processing performed by an image processing apparatus according to the second embodiment.

FIG. 17A and FIG. 17B are flowcharts illustrating a flow of an example of a region extraction processing that is performed by the image processing apparatus 100 according to the second embodiment. The region extraction processing illustrated in FIG. 17A and FIG. 17B is performed when a user inputs an instruction to perform the region extraction processing to the processing circuitry 105 through the input interface 103 in a state in which medical image data to be processed is stored in the storage circuit 102.

Figure 18:
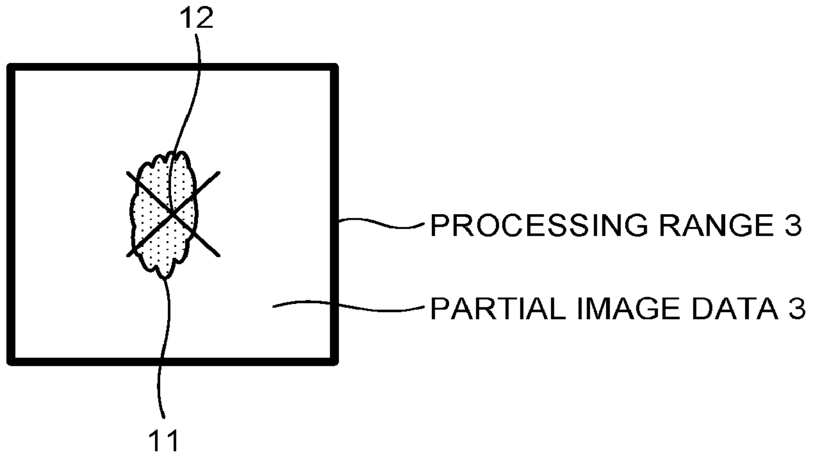
FIG. 18 is a diagram for explaining an example of processing performed by the image processing apparatus according to the second embodiment.

As illustrated in FIG. 17A and FIG. 17B, in the second embodiment, the image processing apparatus 100 performs processing at steps S201 to S211 between the processing at step S101 and the processing at step S102. Moreover, the processing at step S201 to S209 is similar to the processing at steps S102 to S110. However, in the processing at steps S201 to S209, the fixed size 2 that is smaller than the fixed size 1 is used, and in the processing at steps S102 to S110, the fixed size 1 is used. FIG. 18 is a diagram for explaining an example of processing performed by the image processing apparatus 100 according to the second embodiment.

As illustrated in FIG. 17A and FIG. 18, the first extracting function 105*a* regards a three-dimensional image range of a predetermined fixed size (fixed size 2) including the specified point 12 on the medical image data, and extracts coordinates of the processing range 3, and acquires three-dimensional partial image data 3 in the processing range 3 (step S201). The processing range 3 is, for example, a range indicated by a cube or a cuboid in a predetermined size in which the specified point 12 is set at its center position. That is, the processing range 3 is a range defined by 6 planes of a cube of a cuboid in a predetermined size. At step S201, based on that one side of the processing range 3 is predetermined, and that directions of 12 sides of the processing range 3 in an image coordinate system, which is a three-dimensional orthogonal (X, Y, Z) coordinate system, are respectively predetermined, the first extracting function 105*a* may acquire coordinates of a single vertex of the processing range 3 as coordinates enabling to define the processing range 3.

Next, the first extracting function 105*a* acquires an inference probability map 3 corresponding to the partial image data 3 by using an inference model that has been trained in advance as a region extracting means to extract a region of interest from the medical image data (step S202). An example of processing at step S202 will be explained. For example, the inference model is stored in the storage circuit 102 in advance. The inference model is a neural network that outputs, when the partial image data 3 in the predetermined fixed size 2 is input, the inference probability map 3, which is a map indicating a probability that respective pixels of the partial image data 3 are a pixel included in the region of interest 11.

At step S202, the first extracting function 105*a* acquires the inference model stored in the storage circuit 102. The first extracting function 105*a* then inputs the partial image data into the acquired inference model, to acquired the inference probability map 3 that is output from the inference model.

At step S202, the first extracting function 105*a* may resize (isotropically rescale) the partial image data 1 to make pixel spacing of the partial image data 3 be lxlxl [mm], and may input the isotropically rescaled image data obtained as a result of resizing to the inference model. In this case, coordinates of the specified point 12 are converted into coordinates corresponding to the isotropically rescaled image data.

Next, the first extracting function 105*a* sets an initial value "0.5" to a threshold (binary threshold) $T_3$ used at step S204 described later (step S203). The initial value is not limited to "0.5". As long as it is a value larger than 0.0 and smaller than 1.0, any value may be used as the initial value.

Next, the first extracting function 105*a* performs binary processing with respect to the inference probability map 3 acquired at step S202 using the binary threshold $T_3$, to acquire an extraction region 3 (step S204).

Next, the first extracting function 105*a* calculates the size of the extraction region 3 extracted at step S204, and determines whether the calculated size is equal to or larger than a predetermined minimum size (step S205). For example, as the size of the extraction region 3, the number of pixels or the volume of the extraction region 3 can be considered. Furthermore, the minimum size may be set by a user.

When the size of the extraction region 3 is equal to or larger than the minimum size (step S205: YES), the first extracting function 105*a* proceeds to step S207. On the other hand, when the size of the extraction region 3 is smaller than the minimum size (step S205: NO), the first extracting function 105*a* reduces the binary threshold $T_3$ in accordance with a predetermined rule (step S206). The predetermined rule is, for example, a rule of multiplying the binary threshold $T_3$ by "0.2".

Subsequently, the first extracting function 105*a* returns to step S204. In this case, at step S204, the first extracting function 105*a* performs binary processing with respect to the inference probability map 3 acquired at step S202 using the binary threshold $T_3$ reduced at step S206, to acquire the extraction region 3. The first extracting function 105*a* performs processing at step S205 and later again. When the binary threshold $T_3$ reduced at step S206 becomes smaller than a predetermined minimum threshold (for example, 0.02), the first extracting function 105*a* sets the minimum threshold to the binary threshold 13, and proceeds to step S207 from step S206 without returning to step S204 from step S206.

By the processing at steps S205 and S206, it is possible to increase the possibility of extracting the extraction region 3 in a size equal to or larger than the minimum size. The processing at steps S205 and S206 may be omitted.

As described above, the first extracting function 105*a* extracts the extraction region 3 that is estimated as the region of interest 11 from the partial image data included in the processing range 3 including the specified point 12 of the medical image data. The processing range 3 is one example of the third processing range. The partial image data 3 is one example of third partial image data. The extraction region 3 is one example of a third extraction region. Moreover, the first extracting function 105*a* acquires the inference probability map 3 that is obtained by calculating a probability that respective pixels of the partial image data 3 are a pixel included in the region of interest 11, and extracts the extraction region by binarizing the inference probability map 3. The inference probability map 3 is one example of a third inference probability map.

Moreover, as described above, when the size of the extraction region 3 is smaller than a predetermined size (minimum size), the first extracting function 105*a* reduces the binary threshold $T_3$ used when the inference probability map 3 is binarized in accordance with a predetermined rule, and acquires the extraction region 3 by binarizing the inference probability map 3 again using the reduced binary threshold $T_3$.

Next, the removing function 105*b* determines whether the extraction region 3 includes plural partial regions that are not connected to each other (step S207).

When the extraction region 3 does not include plural partial regions that are not connected to each other (step S207: NO), that is, when the extraction region 3 is a single region, the removing function 105*b* proceeds to step S102 illustrated in FIG. 17B.

On the other hand, when the extraction region 3 includes plural partial regions that are not connected to each other (step S207: YES), the removing function 105*b* leaves only a specific partial region out of the plural partial regions, and remove the other partial region (step S208). The removing function 105*b* performs processing similar to the processing at step S109 according to the first embodiment at step S208 according to the second embodiment.

By the processing at step S208, it is possible to remove an unnecessary partial region that has a high possibility of erroneous extraction of extracting a region that is not the region of interest 11 by mistake. Moreover, as a result of removing the unnecessary partial region having a high possibility of erroneous extraction, it is possible to suppress increase of computational time because of an increased processing range based on the region erroneously extracted.

Next, the first extracting function 105*a* sets a value of probability set to a pixel other than pixels corresponding to pixels of the extraction region 3 (new extraction region 3) acquired at step S208 out of all of pixels of the inference probability map 3 acquired at step S202 to "0.0" (step S209). At step S209, the first extracting function 105*a* does not change a probability set to a pixel corresponding to the pixel of the extraction region 3 acquired at step S208 out of all of pixels of the inference probability map 3 acquired at step S202. Thus, the first extracting function 105*a* acquires the new inference probability map 3. When the inference probability map 3 is acquired at step S209, in the processing at step S210 and later, the inference probability map 3 that is acquired at step S209 is used instead of the inference probability map 3 acquired at step S202. The processing at steps S207 to S209 may be omitted.

There is a case in which the extraction region 1 is only a part of the region of interest 11. That is, there is a case in which the first extracting function 105*a* does not extract the entire region of interest 11. Accordingly, the determining function 105*c* determines whether the region of interest 11 is present beyond the processing range 3 (step S210). The determining method at step S210 is, for example, similar to the determining method at step S112.

When the region of interest 11 is not present beyond the processing range 3 (step S210: NO), the first extracting function 105*a* determines the extraction region 3 as the final extraction region (step S211), and ends the region extraction processing. In the second embodiment, the display control function 105*g* controls the display 104 to display the final extraction region similarly to the first embodiment.

On the other hand, when the region of interest 11 is present beyond the processing range 3 (step S210: YES). the image processing apparatus 100 proceeds to step S102 as illustrated in FIG. 17B. The image processing apparatus 100 performs processing at step S102 and later, similarly to the first embodiment.

The region extraction processing according to the second embodiment has been explained. In the region extraction processing according to the second embodiment, the first extracting function 105*a* extracts the extraction region 3 that is estimated as the region of interest 11 from the partial image data included in the processing range 3 that is smaller than the processing range 1 including the specified point 12 of the medical image data. The first extracting function 105*a* extracts the extraction region 1 when it is determined that the extraction region 3 is a part of the region of interest 11. Moreover, the display control function 105*g* displays the extraction region 3 on the display 104 when it is determined that the extraction region 3 is the entire region of the region of interest 11.

As above, the image processing apparatus 100 according to the second embodiment has been explained. In the second embodiment, the processing at steps S201 to S211 is performed prior to step S102. This enables to increase the region extraction accuracy of the region of interest 11 that is smaller than the fixed size 3.

First Modification of Second Embodiment

Next, the image processing apparatus 100 according to a first modification of the second embodiment will be explained. In the following explanation, a configuration different between the second embodiment and the first modification of the second embodiment will be mainly explained, and explanation of an identical or a similar configuration may be omitted. Moreover, in the following explanation, identical signs are assigned to configurations identical or similar to those of the second embodiment, and explanation thereof may be omitted.

In the second embodiment described above, in the inference probability map 3 and the inference probability map 1, different probabilities are acquired at corresponding pixel positions. By using both of these different probabilities (for example, by integrating two different probabilities), a more reliable probability can be obtained. Accordingly, the image processing apparatus 100 according to the first modification of the second embodiment explained below performs processing explained below to obtain a more reliable probability.

Figure 19A:
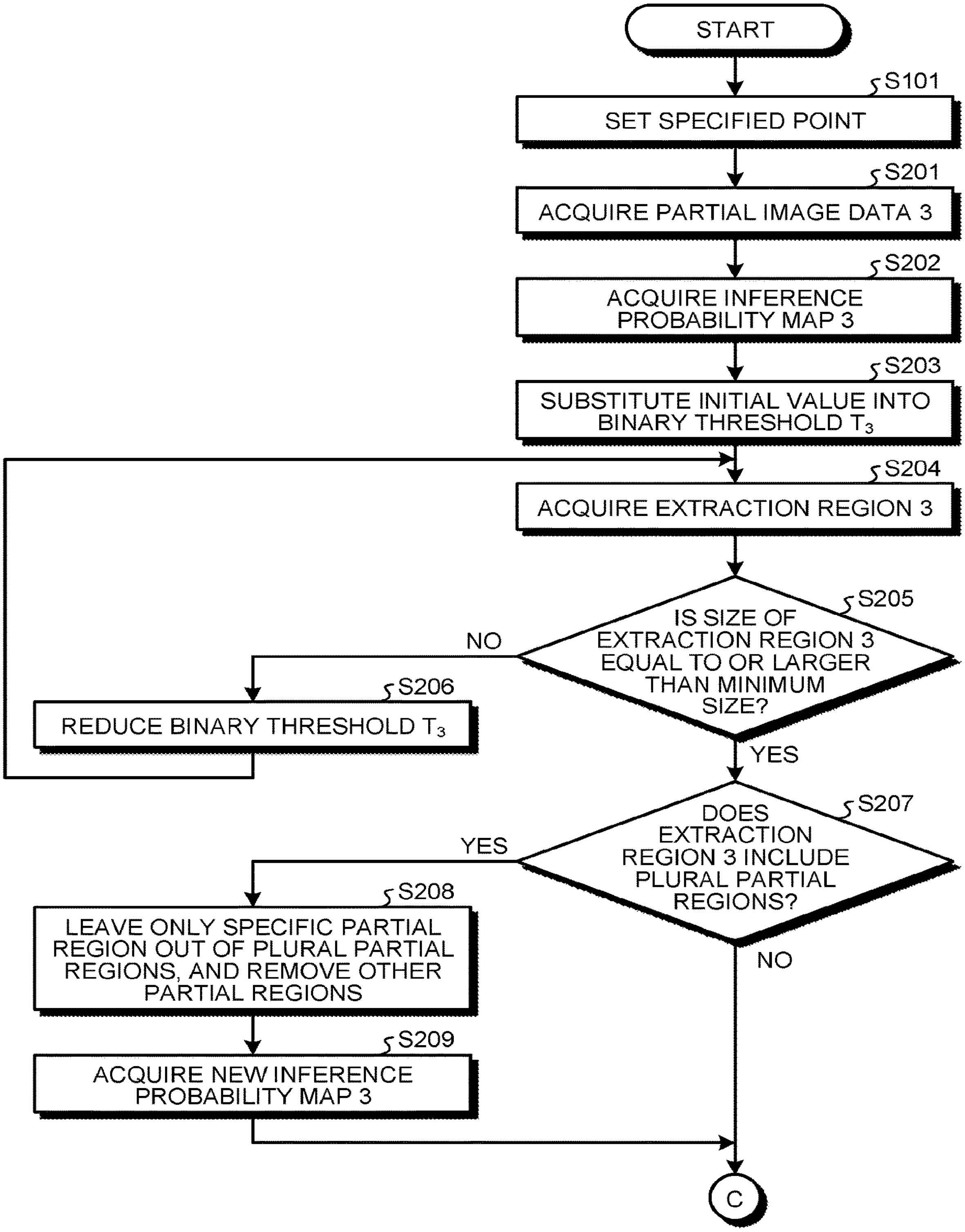
FIG. 19A is a flowchart illustrating a flow of an example of region extraction processing performed by an image processing apparatus according to a first modification of the second embodiment.
Figure 19B:
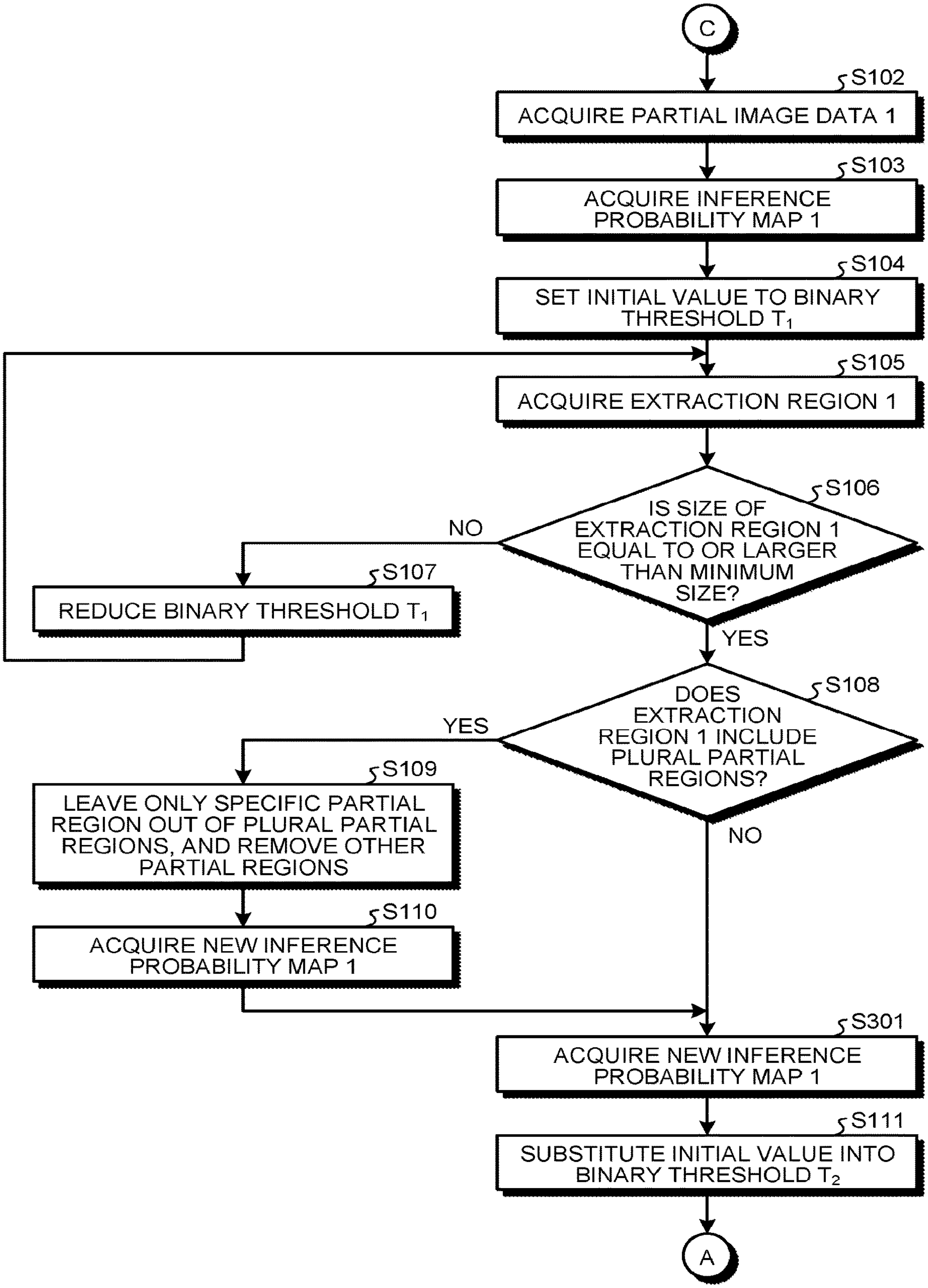
FIG. 19B is a flowchart illustrating a flow of an example of the region extraction processing performed by the image processing apparatus according to the first modification of the second embodiment.

FIG. 19A and FIG. 19B are flowcharts illustrating a flow of an example of region extraction processing performed by the image processing apparatus 100 according to the first modification of the second embodiment. The region extraction processing illustrated in FIG. 19A and FIG. 19B is performed when a user inputs an instruction to perform the region extraction processing into the processing circuitry 105 through the input interface 103 in a state in which medical image data to be processed is stored in the storage circuit 102.

As illustrated in FIG. 19A, in the first modification of the second embodiment, the image processing apparatus 100 performs processing at steps S201 to S209 similarly to the second embodiment. The image processing apparatus 100 then proceeds to step S102 as illustrated in FIG. 19B without performing the processing at steps S210 and S211. The image processing apparatus 100 then performs the processing of steps S102 to S110.

When the extraction region 1 does not include plural partial regions that are not connected to each other (step S108: NO), and when the processing at step S110 is completed, the integrating function 105f proceeds to step S301. At step S301, the integrating function 105f integrates the inference probability map 3 and the inference probability map 1 such that positions thereof are aligned with each other based on respective coordinates, to acquire the new inference probability map 1. For example, the integrating function 105f integrates the inference probability map 3 and the inference probability map 1 at step S301 by a similar method as the method of acquiring the new inference probability map 1 by integrating the inference probability map 1 and the inference probability map 2 at step S116, to thereby acquire the new inference probability map 1.

The image processing apparatus 100 then proceeds to step S111. Subsequently, the image processing apparatus 100 performs the processing at step S111 and later, similarly to the second embodiment.

As above, the image processing apparatus 100 according to the first modification of the second embodiment has been explained. According to the image processing apparatus 100 according to the first modification of the second embodiment, by using both the inference probability map 3 and the inference probability map 1, the extraction accuracy of the region of interest 11 smaller than the fixed size 1 is expected to be improved.

Second Modification of Second Embodiment

Next, the image processing apparatus 100 according to a second modification of the second embodiment will be explained. In the following explanation, a configuration different between the second embodiment and the second modification of the second embodiment will be mainly explained, and explanation of an identical or similar configuration may be omitted. Furthermore, in the following explanation, identical signs are assigned to configurations identical or similar to those of the second embodiment, and explanation thereof may be omitted.

In the second embodiment, a case in which the fixed size 2 smaller than the fixed size 1 is used has been explained. That is, in the second embodiment, the processing range 3 in the fixed size 2 is smaller than the processing range 1 of the fixed size 1. On the other hand, in the second modification of the second embodiment, the fixed size 2 is supposed to be larger than the fixed size 1. That is, in the second modification of the second embodiment, the processing range 3 in the fixed size 2 is larger than the processing range 1 in the fixed size 1.

In the second modification of the second embodiment, the image processing apparatus 100 does not perform the processing at steps S210 and S211. Specifically, the first extracting function 105a performs determining processing of determining whether the extraction region 3 fits inside the processing range 1 in the fixed size 1, instead of the processing at steps S210 and S211.

When the extraction region 3 fits inside the processing range 1 in the fixed size 1, the image processing apparatus 100 performs the processing at step S102 and later illustrated in FIG. 17B using not the processing range 3 but the processing range 1 that is smaller than the processing range 3. That is, the first extracting function 105a extracts the extraction region 1 using the processing range 1 when the extraction region 3 fits within the processing range 1.

On the other hand, when the extraction region 3 does not fit inside within the processing range 1 in the fixed size 1, the image processing apparatus 100 performs the processing similar to the processing at step S104 and later illustrated in FIG. 17B such that a subject to be processed is to be not the extraction region 1 but the extraction region 3, by using the processing range 3 instead of the processing range 1.

As above, the image processing apparatus 100 according to the second modification of the second embodiment has been explained. The image processing apparatus 100 according to the second modification of the second embodiment performs the processing at step S102 and later illustrated in FIG. 17B using not the processing range 3 but the processing range 1 that is smaller than the processing range 3 when the processing range 3 fits within the processing range 1 in the fixed size 1. Therefore, it is possible to improve the extraction accuracy of the region of interest 11.

A term "processor" used in the above explanation signifies a circuit, such as a central processing unit (CPU), a graphical processing unit (GPU), an application specific integrated circuit (ASIC), a programmable logic device (for example, simple programmable logic device (SPLD), complex programmable logic device (CPLD)), and a field programmable gate array (FPGA). The processor implements a function by reading and executing a program stored in the storage circuit. Moreover, instead of storing a program in the storage circuit, it may be configured to directly install a program in a circuit of the processor. In this case, the processor implements the function by reading the program installed in the circuit, and by executing the read program. The respective processors of the present embodiment are not limited to be configured as a single circuit for each processor, but may be configured by combining plural independent circuits as one processor, to implement its function.

Other Embodiments

Other than the embodiments described above, it may be implemented by various different forms.

For example, the respective components of the respective devices illustrated are of functional concept, and it is not necessarily required to be configured physically as illustrated. That is, specific forms of distribution and integration of the respective devices are not limited to the ones illustrated, and all or some thereof can be configured to be distributed or integrated functionally or physically in arbitrary units according to various kinds of loads, usage conditions, and the like. Furthermore, as for the respective processing functions performed by the respective devices, all or an arbitrary part thereof can be implemented by a CPU and a computer program that is analyzed and executed by the CPU, or can be implemented as hardware by wired logic.

Moreover, out of the respective processing explained in the above embodiments, all or some of processing explained to be performed automatically can also be performed manually, or all or some of processing explained to be performed manually can also be performed automatically by a publicly-known method. Besides, the procedure of processing, the procedure of controlling, the specific names, and the information including various kinds of data and parameters described in the above document or in the drawings can be arbitrarily changed, unless otherwise specified.

Moreover, the method explained in the above embodiments can be implemented by executing a program that has been prepared in advance by a computer such as a personal computer and a workstation. This program can be distributed through a network such as the Internet. Furthermore, this control program can be recorded on a computer-readable non-volatile recording medium, such as a hard disk, a flexible disk (FD), a compact-disk read-only memory (CD-ROM), a magneto optical disk (MO), and a digital versatile disk (DVD), and can be executed by being read by a computer from the recording medium.

According to at least one of the embodiments, a region of interest captured in medical image data can be extracted highly accurately and at high speed.

Some embodiments have been explained, but these embodiments are presented as an example, and are not intended to limit the scope of the invention. These embodiments can be implemented in various other forms, and various omission, replacement, change, and combination of embodiments are possible within a range not departing from the gist of the invention. These embodiments and their modifications are included in the scope and the gist of the invention, and is included in the range of the invention described in claims and its equivalence similarly.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An image processing apparatus that extracts a region of interest of medical significance, the region of interest including a specified point on medical image data, the apparatus comprising:

processing circuitry that extracts a first extraction region estimated as the region of interest of medical significance from first partial image data included in a first processing range that includes the specified point of the medical image data, and that extracts a second extraction region estimated as the region of interest of medical significance from second partial image data included in a second processing range that is in contact with an edge portion of the first processing range or that includes at least a part of the edge portion, from the medical image data, when the first extraction region extracted from the first partial image data is determined as a part of the region of interest; and a display that displays the first extraction region and the second extraction region, wherein the processing circuitry further acquires a first inference probability map acquired by calculating a probability that respective pixels of the first partial image data are a pixel included in the region of interest, and extracts the first extraction region by binarizing the first inference probability map, or extracts, as the first extraction region, the first inference probability map acquired by calculating the probability that respective pixels of the first partial image data are the pixel included in the region of interest.

2. The image processing apparatus according to claim 1, wherein the processing circuitry further acquires a second inference probability map that is acquired by calculating a probability that respective pixels of the second partial image are a pixel included in the region of interest, and extracts the second extraction region by binarizing the second inference probability map.

3. The image processing apparatus according to claim 2, wherein the processing circuitry further increases, based on a predetermined rule, a binary threshold that is used when the second inference probability map is binarized, and extracts the second extraction region probability map by binarizing the second inference probability map using the increases binary threshold.

4. The image processing apparatus according to claim 1, wherein the processing circuitry further extracts the second inference probability map that is acquired by calculating a probability that respective pixels of the second partial image are a pixel included in the region of interest as the second extraction region.

5. The image processing apparatus according to claim 4, wherein the processing circuitry further acquires a new inference probability map by integrating the first inference probability map and the second inference probability map, and acquires, when there is an overlapping region in the first inference probability map and the second inference probability map, the new inference probability map by using a larger probability out of a first probability of respective pixels in the overlapping region of the first inference probability map and a second probability of respective pixels in the overlapping region of the second inference probability map as a probability of respective pixels of a region corresponding to the overlapping region in the new inference probability map.

6. The image processing apparatus according to claim 4, wherein the processing circuitry further acquires a new inference probability map by integrating the first inference probability map and the second inference probability map, and acquires, when there is an overlapping region in the first inference probability map and the second inference probability map, the new inference probability map by using an average value of a first probability of respective pixels in the overlapping region of the first inference probability map and a second probability of respective pixels in the overlapping region of the second inference probability map as a probability of respective pixels of a region corresponding to the overlapping region in the new inference probability map.

7. The image processing apparatus according to claim 4, wherein the processing circuitry further acquires a new inference probability map by integrating the first inference probability map and the second inference probability map, and calculates, when there is an overlapping region in the first inference probability map and the second inference probability map, a probability of respective pixels of a region corresponding to the overlapping region in the new inference probability map by summing up a first value and a second value, the first value obtained by multiplying a first probability of respective pixels in the overlapping region of the first inference probability map by a first weight that decreases as the first weight departs farther from a center of the first processing range, the second value obtained by multiplying a second probability of respective pixels in the overlapping region of the second inference probability map by a second weight that decreases as the second weight departs farther from a center of the second processing range.

8. The image processing apparatus according to claim 1, wherein the processing circuitry further determines whether at least a part of the first extraction region is a part of the region of interest by determining whether at least a part of the first extraction region is present at the edge portion of the first processing range.

9. The image processing apparatus according to claim 1, wherein the processing circuitry further determines whether the first extraction region is a part of the region of interest by determining whether a statistical amount of a probability of the first inference probability map present at the edge portion of the first processing range is equal to or larger than a predetermined value.

10. The image processing apparatus according to claim 1, wherein the processing circuitry further determines whether the first extraction region is a part of the region of interest, acquires a direction in which the second processing range is set with reference to the first processing range when the first extraction region is determined as a part of the region of interest, and sets the second processing range at a position that is shifted from the first processing range by a predetermined distance in the acquired direction, and extracts the second extraction region from the second partial image data included in the set second processing range.

11. The image processing apparatus according to claim 10, wherein the processing circuitry further acquires, as the direction in which the second processing range is set with reference to the first processing range, a direction in which the first extraction region is determined as a part of the region of interest based on whether the first extraction region is determined as a part of the region of interest in any direction relative to a center of the first processing range.

12. The image processing apparatus according to claim 1, wherein the processing circuitry further sets the second processing range at a position respectively shifted by a predetermined distance in all of directions in which the edge portion of the first processing range is present, and extracts the second extraction region from the second partial image data included in the set second processing range.

13. The image processing apparatus according to claim 1, wherein the processing circuitry further removes, when the first extraction region includes a plurality of partial regions that are not connected to each other, a partial region that does not include the specified point out of the partial regions.

14. The image processing apparatus according to claim 1, wherein the processing circuitry further calculates, when the first extraction region includes a plurality of partial regions that are not connected to each other, a center of gravity of each of the partial regions, and removes a partial region other than a particular partial region, the center of gravity of which is closest to the specified point.

15. The image processing apparatus according to claim 1, wherein the processing circuitry further removes, when the first extraction region includes a plurality of partial regions that are not connected to each other, a partial region other than a particular partial region, a center of bounding rectangle of which is closest to the specified point, out of the partial regions.

16. The image processing apparatus according to claim 1, wherein the processing circuitry further removes, when the first extraction region includes a plurality of partial regions that are not connected to each other, a partial region other than a particular partial region, a size of which is largest out of the partial regions.

17. The image processing apparatus according to claim 1, wherein the processing circuitry further reduces, based on a predetermined rule, a binary threshold that is used when the first inference probability map is binarized when a size of the first extraction region is smaller than a predetermined size, and extracts the first extraction region by binarizing the first inference probability map again using the reduced binary threshold.

18. The image processing apparatus according to claim 1, wherein the processing circuitry further extracts a third extraction region estimated as the region of interest from third partial image data included in a third processing range that is smaller than the first processing range including the specified point of the medical image data, extracts the first extraction region when it is determined that the third extraction region is a part of the region of interest, and causes the display to display the third extraction region when it is determined that the third extraction region is an entire region of the region of interest.

19. The image processing apparatus according to claim 18, wherein the processing circuitry further acquires the first inference probability map acquired by calculating a probability that respective pixels of the first partial image data are a pixel included in the region of interest, and a third inference probability map acquired by calculating a probability that respective pixels of the third partial image data are a pixel included in the region of interest, and acquires a new inference probability map by integrating the first inference probability map and the third inference probability map.

20. The image processing apparatus according to claim 1, wherein the processing circuitry further extracts a third extraction region estimated as the region of interest from third partial image data included in a third processing range that is larger than the first processing range including the specified point of the medical image data, and extracts the first extraction region using the first processing range when the third extraction region fits within the first processing range.

21. The image processing apparatus according to claim 1, wherein the processing circuitry further acquires a new extraction region by integrating the first extraction region and the second extraction region.

22. The image processing apparatus according to claim 1, wherein the processing circuitry further sets the second processing range by using region information that indicates at least one of a region in which the region of interest is present and a region in which the region of interest is not present, and extracts the second extraction region estimated as the region of interest from the second partial image data that is included in the set second processing range.

23. An image processing method of extracting a region of interest of medical significance, the region of interest including a specified point on medical image data, the method comprising:

extracting a first extraction region estimated as the region of interest of medical significance from first partial image data included in a first processing range that includes the specified point of the medical image data;

extracting a second extraction region estimated as the region of interest of medical significance from second partial image data included in a second processing range that is in contact with an edge portion of the first processing range or that includes at least a part of the edge portion, from the medical image data, when the first extraction region is determined as a part of the region of interest; and causing a display to display the first extraction region and the second extraction region, wherein the extracting the first extraction region comprises acquiring a first inference probability map acquired by calculating a probability that respective pixels of the first partial image data are a pixel included in the region of interest, and extracting the first extraction region by binarizing the first inference probability map, or extracting, as the first extraction region, the first inference probability map acquired by calculating the probability that respective pixels of the first partial image data are the pixel included in the region of interest.

24. A non-transitory computer-readable recording medium that records a program causing a computer to extract a region of interest of medical significance, the region of interest including a specified point on medical image data, the program causing the computer to execute:

extracting a first extraction region estimated as the region of interest of medical significance from first partial image data included in a first processing range that includes the specified point of the medical image data;

extracting a second extraction region estimated as the region of interest of medical significance from second partial image data included in a second processing range that is in contact with an edge portion of the first processing range or that includes at least a part of the edge portion, from the medical image data, when the first extraction region is determined as a part of the region of interest; and causing a display to display the first extraction region and the second extraction region, wherein the extracting the first extraction region comprises acquiring a first inference probability map acquired by calculating a probability that respective pixels of the first partial image data are a pixel included in the region of interest, and extracting the first extraction region by binarizing the first inference probability map, or extracting, as the first extraction region, the first inference probability map acquired by calculating the probability that respective pixels of the first partial image data are the pixel included in the region of interest.

* * * * *